(12) United States Patent
Long

(10) Patent No.: US 6,918,906 B2
(45) Date of Patent: Jul. 19, 2005

(54) ENDOSCOPIC ABLATION SYSTEM WITH IMPROVED ELECTRODE GEOMETRY

(76) Inventor: Gary L. Long, 3722 Pleasant St., Mariemont, OH (US) 45227

( * ) Notice: Subject to any disclaimer, the term of this patent is extended or adjusted under 35 U.S.C. 154(b) by 34 days.

(21) Appl. No.: 10/105,722

(22) Filed: Mar. 25, 2002

(65) Prior Publication Data

US 2002/0147447 A1 Oct. 10, 2002

Related U.S. Application Data

(60) Provisional application No. 60/280,009, filed on Mar. 30, 2001.

(51) Int. Cl.[7] .............................................. A61B 18/12
(52) U.S. Cl. .......................................... 606/41; 606/49
(58) Field of Search ............................. 600/129, 176, 600/183; 606/41, 45, 47, 49

(56) References Cited

U.S. PATENT DOCUMENTS

| | | |
|---|---|---|
| 874,810 A | 12/1907 | Wappler |
| 4,202,336 A | 5/1980 | van Gerven |
| 4,237,871 A | 12/1980 | Bonnet |
| 4,532,924 A | 8/1985 | Auth et al. |
| 4,582,057 A | 4/1986 | Auth et al. |
| 4,646,722 A | 3/1987 | Silverstein et al. |
| 4,765,331 A | 8/1988 | Petruzzi et al. |
| 4,807,593 A | 2/1989 | Ito |
| 4,819,620 A | 4/1989 | Okutsu |
| 5,025,778 A | 6/1991 | Silverstein et al. |
| 5,080,660 A | 1/1992 | Buelna |
| 5,112,308 A | 5/1992 | Olsen et al. |
| 5,122,138 A | 6/1992 | Manwaring |
| 5,156,151 A | 10/1992 | Imran |
| 5,336,222 A | 8/1994 | Durgin, Jr. et al. |
| 5,500,012 A | 3/1996 | Brucker et al. |
| 5,681,282 A | 10/1997 | Eggers et al. |
| 5,695,448 A | 12/1997 | Kimura et al. |
| 5,697,882 A | 12/1997 | Eggers et al. |
| 5,697,909 A | 12/1997 | Eggers et al. |
| 5,746,696 A | 5/1998 | Kondo |
| 5,749,899 A | 5/1998 | Bardin |
| 5,766,152 A | 6/1998 | Morley et al. |
| 5,766,153 A | 6/1998 | Eggers et al. |
| 5,782,760 A | 7/1998 | Schaer |

(Continued)

FOREIGN PATENT DOCUMENTS

| | | |
|---|---|---|
| JP | 01079017 A | 10/1999 |
| WO | WO 99/00060 A | 1/1999 |
| WO | 01/35846 A1 | 5/1999 |
| WO | 99/35986 A1 | 7/1999 |
| WO | 00/18314 A1 | 4/2000 |
| WO | 00/19926 A1 | 4/2000 |
| WO | 35364 A1 | 6/2000 |
| WO | WO 02/47569 A | 6/2002 |
| WO | WO 02/078557 A1 | 10/2002 |

OTHER PUBLICATIONS

U.S. Appl. 10/105,610, filed Mar. 25, 2002 Entitled: Endoscopic Ablation System with Flexible Coupling.

(Continued)

*Primary Examiner*—Roy D. Gibson
*Assistant Examiner*—Aaron Roane

(57) ABSTRACT

An endoscopic ablation system is provided for use with a flexible endoscope for the ablative treatment of diseased tissue on the interior lining a body lumen. The endoscopic ablation system includes a support member for supporting at least two electrodes that are electrically connected to a RF generator. The electrodes have a shape, size, and spacing that provide ablation between the electrodes, while minimizing ablation of tissue directly underneath the electrodes. The endoscopic ablation system can also include a sheath that fits over a flexible endoscope. A flexible coupling can join the support member to the sheath to facilitate intubation. The support member can include a side opening, and the sheath can include a seal, so that the aspiration means of the endoscope may be used to evacuate the air from inside the body lumen and pull the tissue to be treated into intimate contact with the electrodes.

6 Claims, 19 Drawing Sheets

U.S. PATENT DOCUMENTS

| | | |
|---|---|---|
| 5,782,824 A | 7/1998 | Abela et al. |
| 5,789,047 A | 8/1998 | Sasaki et al. |
| 5,846,182 A | 12/1998 | Wolcott |
| 5,873,877 A | 2/1999 | McGaffigan et al. |
| 5,888,198 A | 3/1999 | Eggers et al. |
| 5,902,272 A | 5/1999 | Eggers et al. |
| 5,941,834 A | 8/1999 | Skladnev et al. |
| 5,961,526 A | 10/1999 | Chu et al. |
| 6,009,877 A | 1/2000 | Edwards |
| 6,010,450 A | 1/2000 | Perkins |
| 6,022,334 A | 2/2000 | Edwards et al. |
| 6,027,499 A | 2/2000 | Johnston et al. |
| 6,056,744 A | 5/2000 | Edwards |
| 6,066,134 A | 5/2000 | Eggers et al. |
| 6,068,603 A | 5/2000 | Suzuki |
| 6,071,233 A | 6/2000 | Ishikawa et al. |
| 6,086,583 A | 7/2000 | Ouchi |
| 6,091,993 A | 7/2000 | Bouchier et al. |
| 6,091,995 A * | 7/2000 | Ingle et al. .................. 607/138 |
| 6,102,434 A | 8/2000 | Ohlert et al. |
| 6,106,521 A | 8/2000 | Blewett et al. |
| 6,120,434 A | 9/2000 | Kimura et al. |
| 6,142,931 A | 11/2000 | Kaji |
| 6,146,378 A | 11/2000 | Mikus et al. |
| 6,149,620 A | 11/2000 | Baker et al. |
| 6,179,832 B1 | 1/2001 | Jones et al. |
| 6,190,381 B1 | 2/2001 | Olsen et al. |
| 6,235,020 B1 | 5/2001 | Cheng et al. |
| 6,238,389 B1 | 5/2001 | Paddock et al. |
| 6,241,702 B1 | 6/2001 | Lundquist et al. |
| 6,241,724 B1 | 6/2001 | Fleischman et al. |
| 6,254,598 B1 | 7/2001 | Edwards et al. |
| 6,258,087 B1 | 7/2001 | Edwards et al. |
| 6,296,638 B1 | 10/2001 | Davison et al. |
| 6,309,379 B1 | 10/2001 | Willard et al. |
| 6,325,798 B1 | 12/2001 | Edwards et al. |
| 6,355,034 B2 | 3/2002 | Cosmescu |
| 6,394,949 B1 * | 5/2002 | Crowley et al. ............ 600/127 |
| 6,402,742 B1 | 6/2002 | Blewett et al. |
| 6,405,732 B1 | 6/2002 | Edwards et al. |
| 6,551,310 B1 | 4/2003 | Ganz et al. |
| 6,645,201 B1 | 11/2003 | Utley et al. |
| 6,740,082 B2 | 5/2004 | Shadduck |
| 2002/0147447 A1 | 10/2002 | Long |
| 2002/0156470 A1 | 10/2002 | Shadduck |
| 2002/0183739 A1 | 12/2002 | Long |
| 2003/0009162 A1 | 1/2003 | Messing et al. |
| 2003/0009163 A1 | 1/2003 | Messing et al. |
| 2003/0181905 A1 | 9/2003 | Long |
| 2003/0216727 A1 | 11/2003 | Long |

OTHER PUBLICATIONS

U.S. Appl. No. 10/105,609, filed Mar. 25, 2002, Entitled: Endoscopic Ablation System with Sealed Sheath.

U.S. Appl. No. 10/105,722, filed Mar. 25, 2002, entitled: Endoscopic Ablation System with Improved Electrode Geometry.

U.S. Appl. No. 10/105,610, filed Mar. 25, 2002, entitled: Electrosurgical Cutting and Coagulation and Suction Instrument.

PCT International Search Report dated Apr. 4, 2003, for international application No. PCT/US02/10185.

PCT Written Opinion regarding PCT/US02/10185.

Guiterrez, Jorge G. et al., A Multipurpose Overtube for Diagnostic and Therapeutic Flexible Fiberoptic Endoscopy. *Gastrointestinal Endoscopy*, 1986, 32(4):274–277.

Rogers, B.H. Gerald et al, An Overtube for the Flexible Fiberoptic Esophagogastroduodenscope. *Gastrointestinal Endoscopy*, 1982, 28(4): 256–57.

EPO Search Report dated Jan. 5, 2004 for related U.S. Appl. No. 10/245,928, European Patent Application No. 03/255838.9.

EPO Search Report dated Jan. 5, 2004 for related U.S. Appl. No. 10/245,928, European Patent Application No. 03/255838.9.

PCT International Search Report PCT/US02/09975 dated Mar. 27, 2003, which corresponds to related U.S. Appl. No. 10/105,609.

EPO Search Report dated Jul. 26, 2004 for related European Patent Application No. EP 04 25 1414.

* cited by examiner

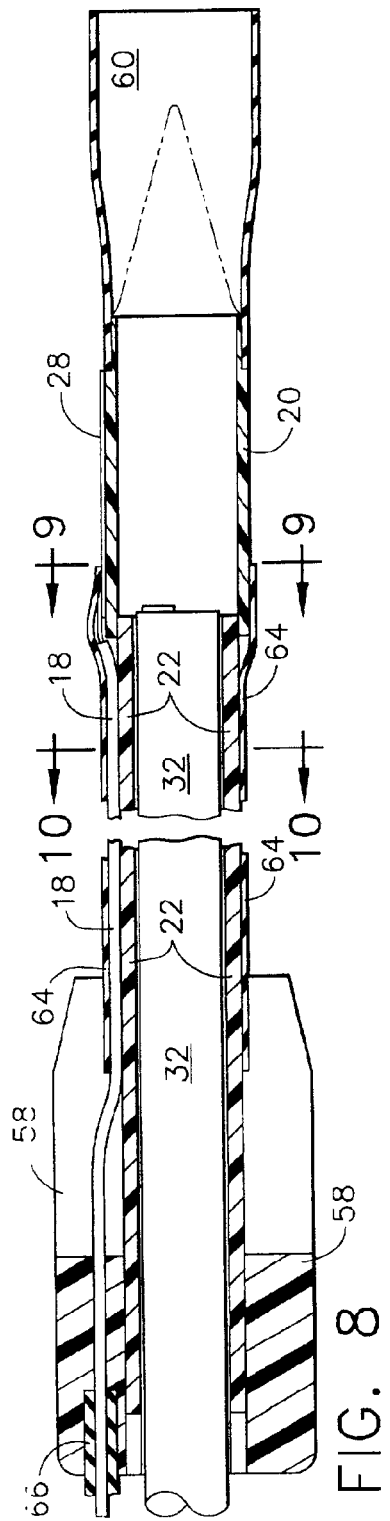
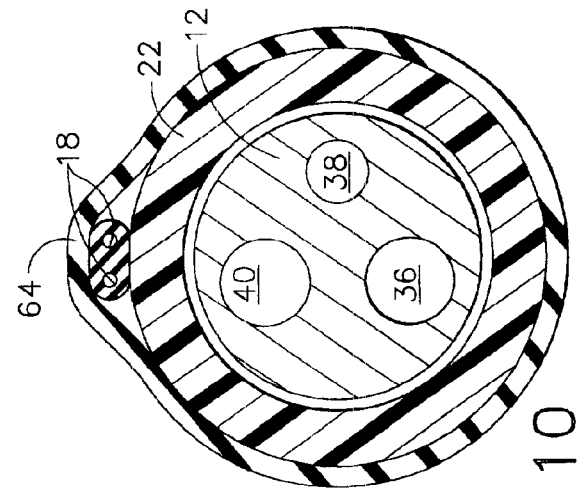
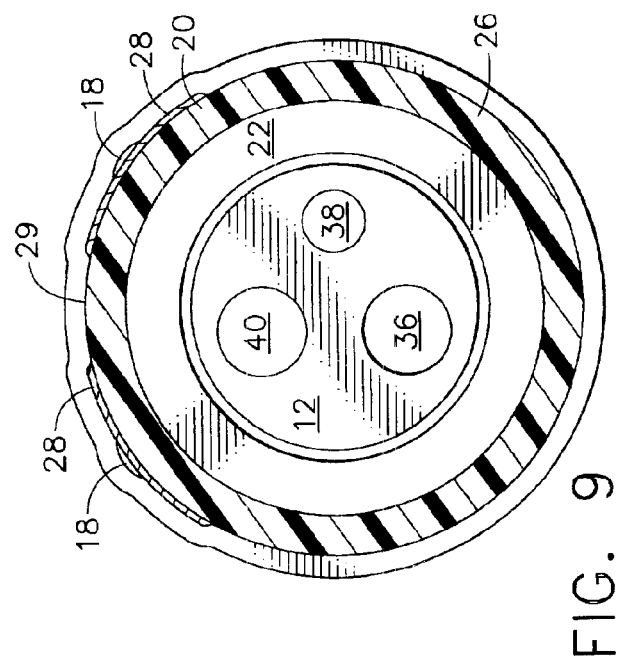

ENDOSCOPIC ABLATION SYSTEM WITH IMPROVED ELECTRODE GEOMETRY

CROSS-REFERENCE TO RELATED PATENT APPLICATIONS

This application claims benefit of provisional application 60/280,009 filed Mar. 30, 2001.

This patent application cross-references and incorporates by reference the following copending, co-filed patent applicacions: "Endoscopic Ablation System with Flexible Coupling", Ser. No. 10/105,610, and "Endoscopic Ablation System with Sealed Sheath", Ser. No. 10/105,609.

FIELD OF THE INVENTION

The present invention relates, in general, to an endoscopic ablation system and, more particularly, to an endoscopic ablation system including a plurality of electrodes adapted to fit over a flexible endoscope and ablate tissue in the esophagus.

BACKGROUND OF THE INVENTION

Gastro-esophageal reflux disease (GERD), which is associated with severe heartburn, affects a substantial portion of the world population. People who experience heartburn at least once a week are reportedly at an increased risk of developing esophageal cancer in their lifetime. When left untreated, chronic GERD can cause the inner lining of the esophagus to change from squamous mucosa to columnar mucosa, which sometimes includes intestinal metaplasia or Barrett's esophagus. Left untreated, Barrett's esophagus can progress to esophageal cancer, for which a common surgical treatment is esophagectomy (removal of the esophagus.)

The first step for stopping the progression of these tissue changes is to reduce the amount of stomach acid that refluxes into the esophagus. This can be done through acid suppression therapy using drugs such as a proton pump inhibitor or surgically, using a surgical procedure such as a Nissan fundoplication. The Nissan fundoplication procedure alters the anatomy of the stomach and esophagus to reduce acid reflux. Once the acid reflux has been treated, the condition of the esophagus is monitored over the patient's lifetime to watch for esophageal cancer.

It has been demonstrated that if the abnormal lining of the esophagus is removed in an anacid environment (i.e., after the patient's GERD has been treated using drugs or surgery), then normal squamous cells will regenerate and the esophageal lining will be restored. Physicians currently use a number of instruments to remove abnormal esophageal tissue, including the Gold Probe™, which is an electrosurgical ablation device available from Boston Scientific, Inc. and which is introduced through the working channel of a flexible endoscope. Another ablation instrument that a physician may use for this purpose is an argon plasma coagulator, which applies a stream of ionized argon gas to facilitate the flow of electrical current. Examples of other ablation modalities incorporated into medical instruments that may be used to ablate tissue in the esophagus include laser and other optical devices such as those used in photodynamic therapy (PDT).

A significant problem with prior art ablation devices used to ablate abnormal regions in the mucosa of the esophagus is the surgeon's lack of adequate control over the size, shape and depth of the treated region. Prior art devices that use electrodes to ablate abnormal regions in the mucosa of the esophagus also provide limited visibility of the treated tissue, thus potentially resulting in damaging adjacent healthy tissue, including healthy tissue under the mucosal layer. Further, problems with prior electrosurgical devices used to ablate tissue in the esophagus arise because such instruments ablate tissue directly beneath the device electrodes. In particular, because the electrodes are opaque, the physician cannot monitor the degree to which tissue under the electrodes is ablated, making it difficult to determine when to stop applying electrical current. Further, since ablated or charred tissue tends to stick to electrodes if treated for too long, removing the instrument may avulse some of the treated tissue away from the wall of the esophagus and cause undesirable bleeding.

The esophagus is a flaccid, tubular organ that has many folds and irregularities on the interior, mucosal lining, especially if diseased. Another significant problem when electrosurgically treating diseased tissue of the esophagus is supporting the walls of the esophagus in order to bring the diseased tissue into intimate contact with the electrodes of the electrosurgical instrument. In addition, the esophagus is not a static structure, but rather contracts frequently due to muscular, peristaltic action. Another consideration when treating the interior lining of the esophagus is post-procedural pain due to tissue trauma associated with passage of instrumentation through the constricted, curved passages of the throat, especially during intubation of the flexible endoscope.

Therefore, an improved medical instrument for treating diseased tissue in the mucosa of the esophagus would provide a physician with the ability to accomplish one or more of the following:

- To position accurately the surgical instrument over the tissue region to be treated, and to do so as atraumatically to the patient as possible.
- To ablate only the tissue in a specific, predefined area, which is visible to the surgeon before and during the ablation (and not treat tissue that is under the treatment electrodes).
- To stop ablation at the appropriate time in order to control ablation depth.
- To support the walls of the body lumen and bring tissue to be treated into intimate contact with treatment electrodes.

SUMMARY OF THE INVENTION

The present invention is an ablation system for electrosurgically treating bodily tissue of a patient. The ablation system comprises at least two electrodes, each of the electrodes having a perimeter P. Adjacent electrodes have adjacent parallel edges spaced apart by a distance d and an ablation index $I=P/d$ is between approximately 1 and 200. In one embodiment of the ablation system of the present invention, the electrodes have a rectangular shape with a width w and a length L, and $P=2(w+L)$. Ablation index I relates to achievable ablation quality. A preferred ablation quality may be obtained using the present invention when the ablation index I is between about 15 and about 35.

The ablation system can further include a viewing window positioned between adjacent electrodes for endoscopic visualization of tissue during ablation, and an ablation cap for creating space in the lumen of a bodily organ. The electrodes can be positioned on the ablation cap, and the viewing window can be a portion of the ablation cap. A RF (radio frequency) generator can be electrically connected to the electrodes, and the operator may actuate the RF generator to ablate tissue endoscopically viewable through the viewing window.

In another embodiment of the present invention, the ablation end cap is hollow and mounted on the distal end of a sheath. The distal end of a flexible endoscope may be inserted through the sheath and at least partially into the ablation cap, and the sheath and the ablation end cap are rotatable with respect to the flexible endoscope.

In yet another embodiment of the present invention, the ablation cap comprises a rigid support member attached to a tapered end cover. The tapered end cover is normally closed and is adapted to open in order to allow passage of the distal end of the endoscope therethrough. In another embodiment, the tapered end cover is normally open and is adapted to allow passage of the distal end of an endoscope therethrough. In yet another embodiment, the tapered end cover is made from a transparent, flexible material, is shaped like a bougie tube, and is adapted to be passed over a guide wire.

In an alternate embodiment of the endoscopic ablation system, the ablation cap comprises a flexible support member and the electrodes are mounted on an electrode sled retractable into a housing attached to the flexible support member. A drive cable is operationally engaged with the electrode sled, so that the operator may actuate the drive cable to move the ablation cap between a retracted position and an extended position when the ablation cap is inserted into the lumen of the bodily organ, and extension of the electrode sled provides structural rigidity to the flexible support member, thereby aiding to support the lumen of the bodily organ.

The endoscopic ablation system of the present invention may further comprise a rotation knob attached at the proximal end of the sheath, and a seal located near the proximal end of the sheath. The seal is adapted to allow passage therethrough of the distal end of the flexible endoscope, so that the sheath and the ablation cap form an enclosure substantially sealed from the air external to the patient, but in fluid communication with the interior of the body lumen.

In an alternate embodiment, the endoscopic ablation system further includes a timer electrically connected in series between the electrodes and the RF generator. The timer electrically connects the output of the RF generator to the electrodes for a predetermined period of time when the operator switches on the RF generator. The endoscopic ablation system may further comprise an actuator, whereby the timer is operable only when the operator actuates the actuator.

A method of ablating tissue on the interior lining of a lumen of a bodily organ is provided. The method comprises providing a flexible endoscope, providing an endoscopic ablation system such as one of the embodiments already described, inserting the distal end of the flexible endoscope into the sheath and at least partially into the ablation cap, intubating the distal end of the flexible endoscope with the sheath and the ablation cap into the lumen of the bodily organ, positioning the viewing window against tissue to be treated, and actuating the RF generator to ablate the tissue against the viewing window.

The present invention has application in conventional and robotic-assisted endoscopic medical procedures.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 8 is a sectional view of the distal end of the endoscopic ablation system illustrated in FIG. 7.

FIG. 9 is a sectional view taken at line 9—9 of the endoscopic ablation system illustrated in FIG. 8.

FIG. 10 is a sectional view taken at line 10—10 of the endoscopic ablation system illustrated in FIG. 8.

DETAILED DESCRIPTION OF THE INVENTION

Figure 1:
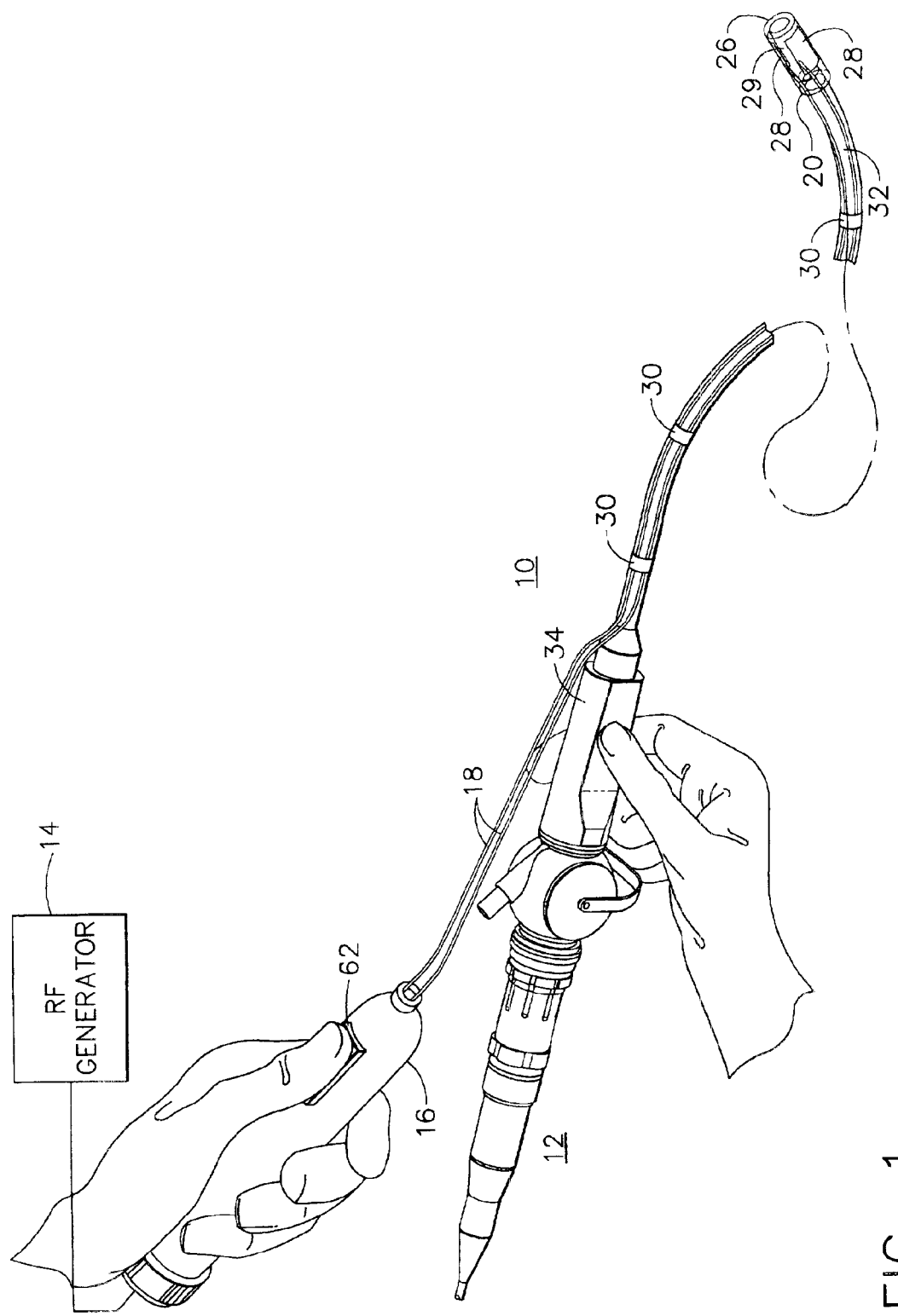
FIG. 1 is an illustration of an endoscopic ablation system according to the present invention mounted on a flexible endoscope.

FIG. 1 shows an endoscopic ablation system 10 according to the present invention mounted on a flexible endoscope 12 (also referred to as endoscope 12), such as the GIF-100 model available from Olympus Corporation. Flexible endoscope 12 includes an endoscope handle 34 and a flexible shaft 32. Endoscopic ablation system 10 generally comprises an ablation cap 20, a plurality of conductors 18, a handpiece 16 having a switch 62, and an RF (radio frequency) generator 14. Ablation cap 20 fits over the distal end of flexible shaft 32 and conductors 18 attach to flexible shaft 32 using a plurality of clips 30. Ablation cap 20 includes a rigid support member 26, a plurality of electrodes 28, and a viewing window 29 positioned between electrodes 28. In this embodiment, rigid support member 26 is made of a transparent material such as polycarbonate and viewing window 29 is the portion of rigid support member 26 between electrodes 18. Manual operation of switch 62 of handpiece 16 electrically connects or disconnects electrodes 18 to RF generator 14. Alternatively, switch 62 may be mounted on, for example, a foot switch (not shown).

RF generator 14 is a conventional, bipolar/monopolar electrosurgical generator such as one of many models commercially available, including Model Number ICC 350, available from Erbe, GmbH. Either the bipolar mode or the monopolar mode may be used for the present invention. When using the bipolar mode with two electrodes 18 on ablation cap 20, one electrode is electrically connected to one bipolar polarity, and the other electrode is electrically connected to the opposite bipolar polarity. If more than two electrodes 18 are used, polarity of electrodes 18 is alternated so that any two adjacent electrodes have opposite polarities. When using the monopolar mode with two or more electrodes 18, a grounding pad is not needed on the patient. Rather, a custom impedance circuit easily made by one skilled in the art, is electrically connected in series with one of conductors 18 that may normally be used with a grounding pad during monopolar electrosurgery. The optimal power level required to operate endoscopic ablation system 10 of the present invention is approximately in the range of 10–50 watts, although endoscopic ablation system 10 is also functional at lower or higher power levels.

Figure 2:
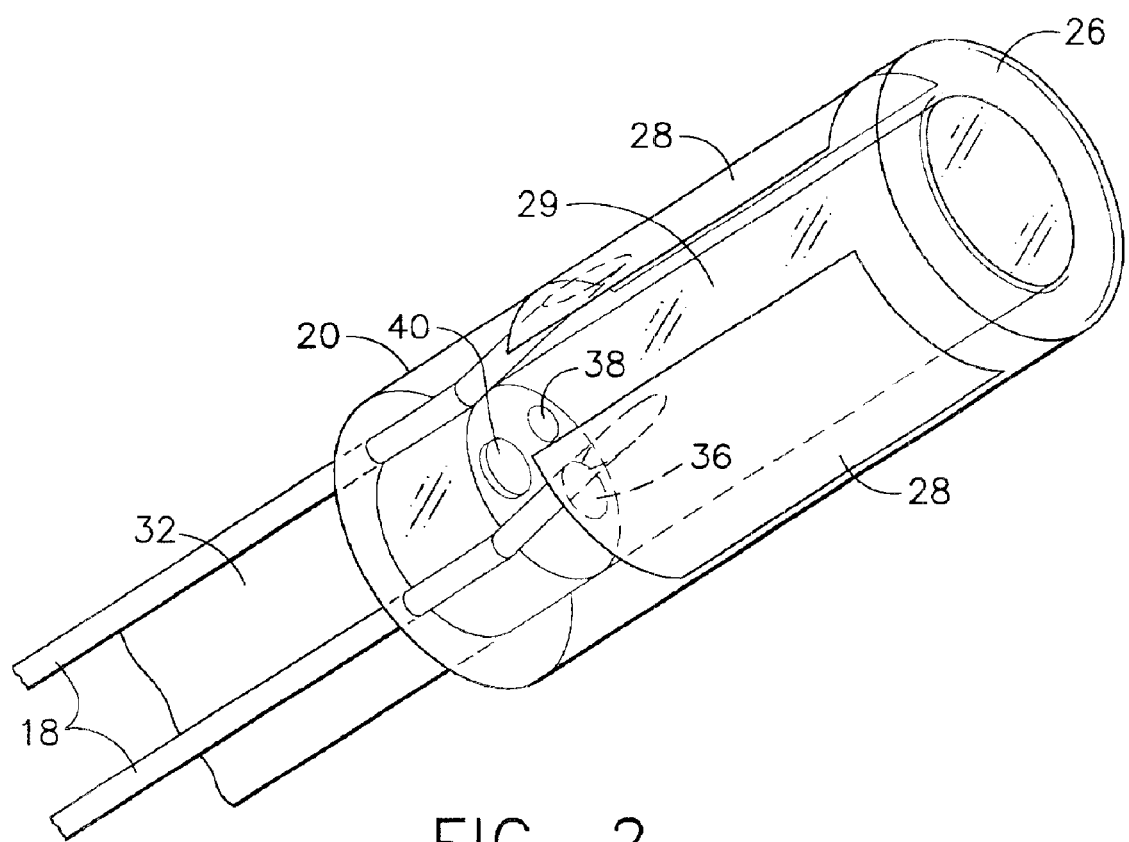
FIG. 2 is an enlarged view of an ablation cap at the distal end of the endoscopic ablation system illustrated in FIG. 1.

FIG. 2 is an enlarged view of ablation cap 20 of endoscopic ablation system 10 shown in FIG. 1. Ablation cap 20 fits securely over the distal end of flexible shaft 32. Electrodes 28 are positioned on the outside surface of rigid support member 26, which has a circular cylinder shape in this embodiment. Rigid support member 26 may also have alternate cylindrical shapes, including shapes in which at least a portion of the cross sectional perimeter is non-arcuate. For example, rigid support member 26 may have a "D-shape" cross-section, where electrodes 28 are positioned on the flat portion of the "D-shape." Conductors 18 are electrically insulated from each other and surrounding structures, except for electrical connections such as to electrodes 28. The distal end of flexible shaft 32 of flexible endoscope 12 includes a light source 40, a viewing port 38, and a working channel 36. Viewing port 38 transmits an image within its field of view to an optical device such as a CCD camera within flexible endoscope 12 so that an operator may view the image on a display monitor (not shown). In the embodiment shown in FIG. 2, the distal end of flexible shaft 32 is proximal to electrodes 28 and viewing window 29, enabling the operator to see tissue between electrodes 28 through viewing window 29.

Figure 3:
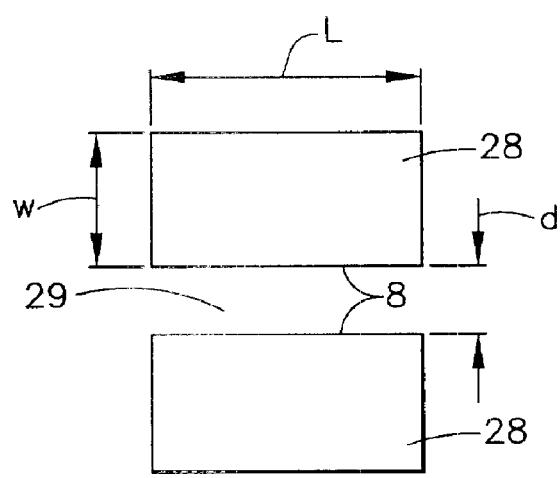
FIG. 3 is a geometric diagram showing the relative size and position of two adjacent electrodes that would be mounted on the ablation cap illustrated in FIG. 2.

FIG. 3 shows the geometric relationship of a particular embodiment of electrodes 28. In this embodiment, two rectangular electrodes 28, also referred to as first and second electrodes, each having a width "w" and a length "L", have parallel, adjacent edges 8 that are separated by a distance "d". This geometric relationship may be used to calculate an ablation index, which has particular significance to the location, size, shape, and depth of ablation achievable, as will be described later. Viewing window 29 (see FIG. 2) is approximately defined by the d×L rectangular area between electrodes 28.

Figure 4:
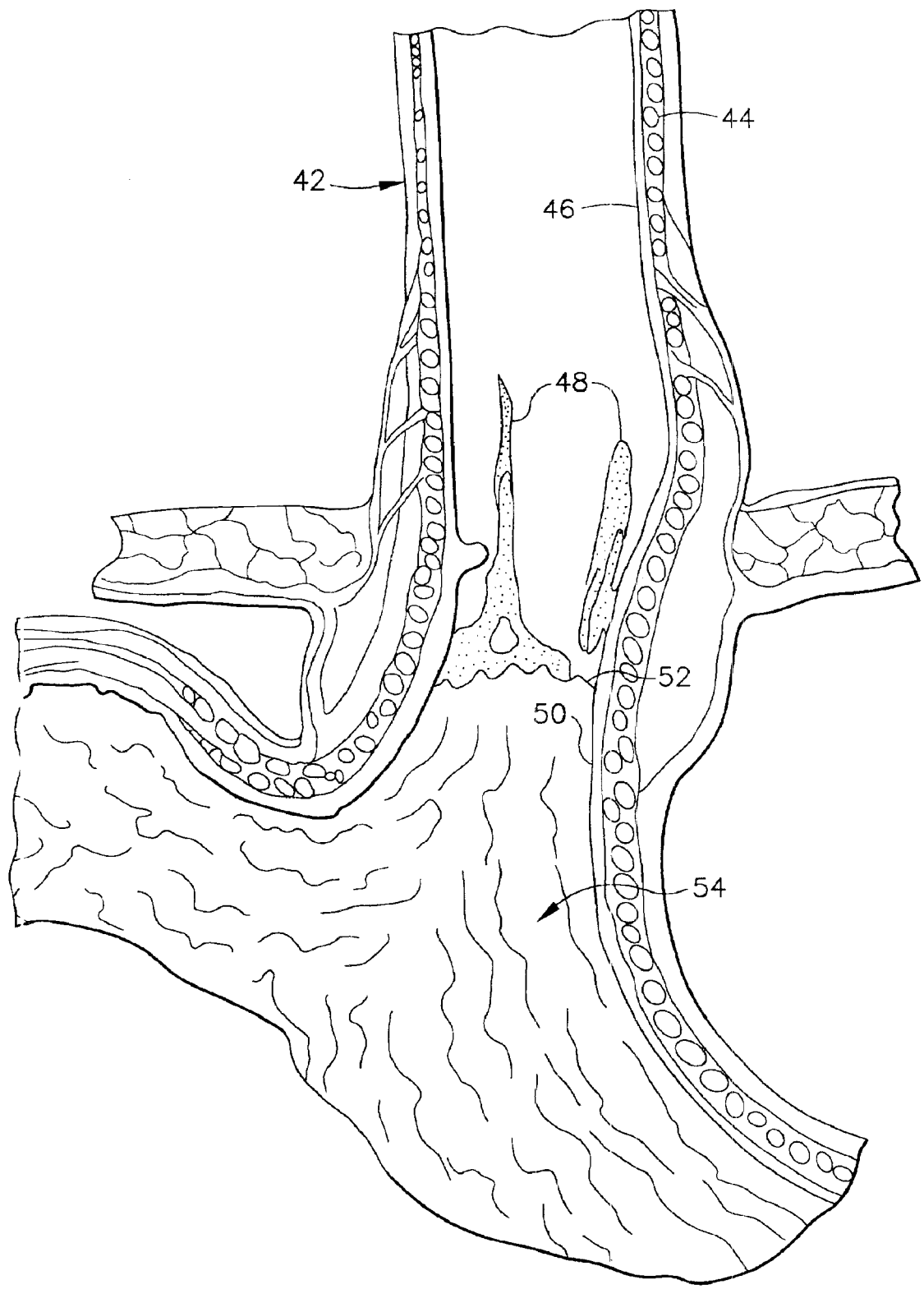
FIG. 4 is a sectional view of the lower esophagus and the upper stomach of a human being.

FIG. 4 is a sectional view of a lower esophagus 42 and the upper portion of a stomach 54 of a human being. Lower esophagus 42 has a mucosal layer 46, a muscular layer 44, and a region of diseased tissue 48. The boundary between mucosal layer 46 of lower esophagus 42 and a gastric mucosa 50 of stomach 54 is a gastro-esophageal junction 52, which is approximately the location for the lower esophageal sphincter (LES). The LES allows food to enter the stomach 54 while preventing the contents of stomach 54 from refluxing into lower esophagus 42 and damaging mucosal layer 46. Diseased tissue 48 can develop when chronic reflux is not treated. In one form, diseased tissue 48 may be, for example, intestinal metaplasia, which is an early stage of Barrett's esophagus.

Figure 5:
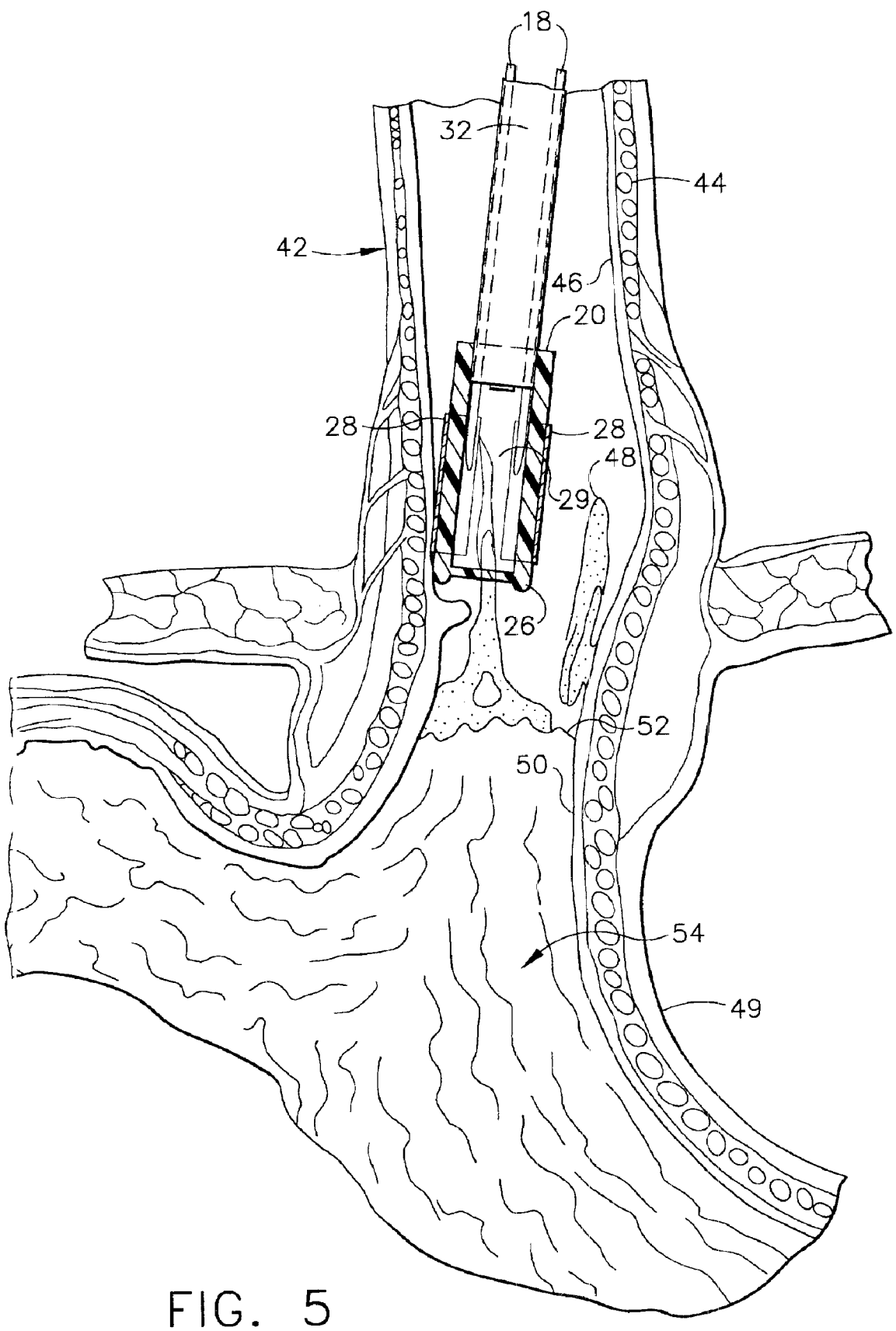
FIG. 5 illustrates the use of the endoscopic ablation system of FIG. 1 to treat tissue at the lower esophagus.

FIG. 5 illustrates the use of endoscopic ablation system 10 to treat diseased tissue 48 in lower esophagus 42. The operator positions ablation cap 20 using endoscopic visualization so that diseased tissue 48 to be treated lies under viewing window 29.

Figure 6:
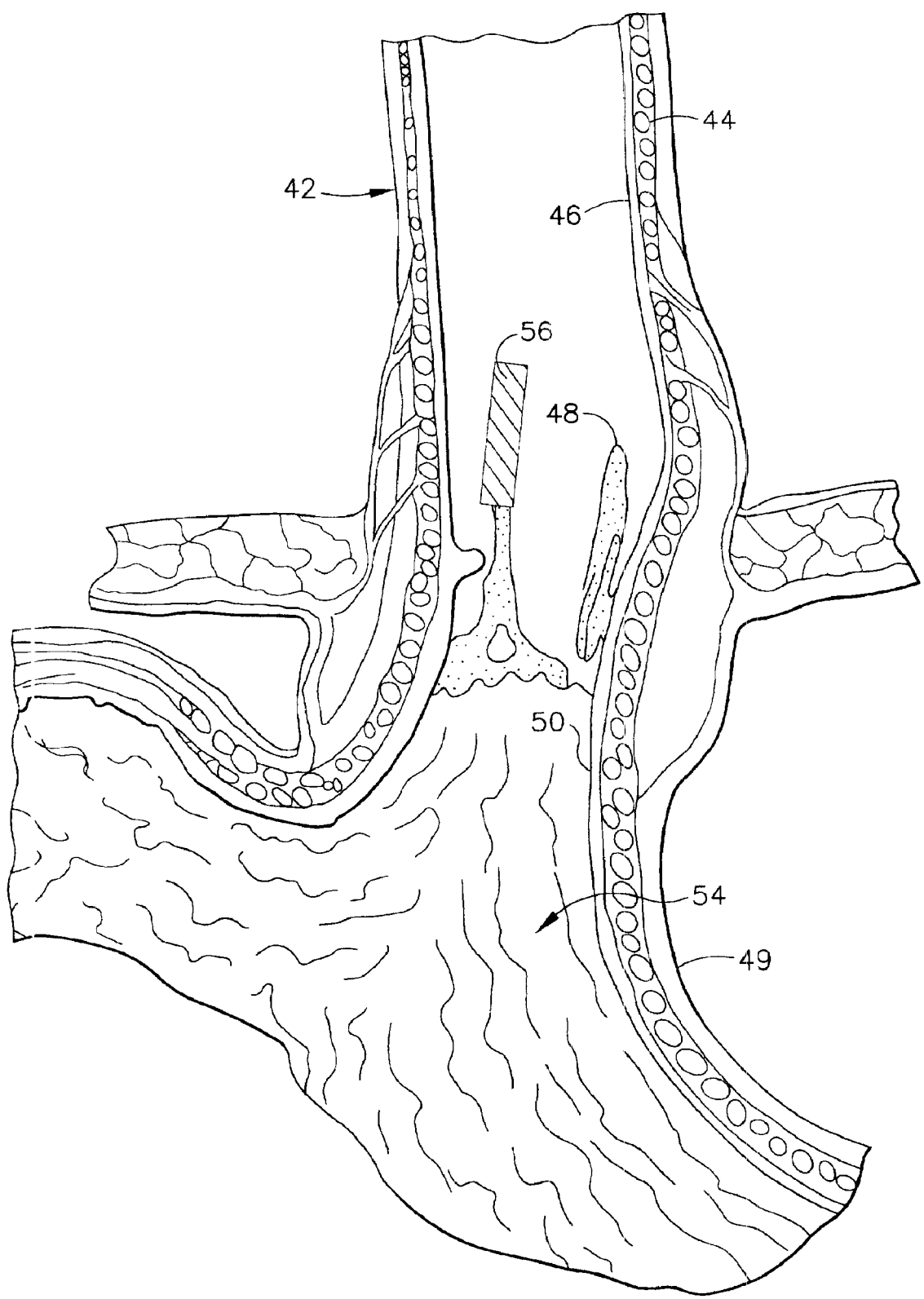
FIG. 6 is sectional view of the lower esophagus showing tissue that has been treated using the endoscopic ablation system of FIG. 1.

FIG. 6 is sectional view of lower esophagus 42 showing tissue that has been treated using endoscopic ablation system 10 according to the present invention. In FIG. 6, the size and shape of the treated tissue 56 substantially corresponds to the size and shape of viewing window 29.

The operator may treat diseased tissue 48 using the embodiment of endoscopic ablation system 10 of the present invention shown in FIGS. 1 and 5 as follows. The operator inserts flexible shaft 32 of endoscope 12 into lower esophagus 42 trans-orally. Rigid support member 26 holds lower esophagus 42 open as the operator uses endoscopic visualization through ablation cap 26 to position electrodes 28 next to the diseased tissue 48 to be treated. Rigid support member 26 opens and supports a portion of the lower esophagus 42 and helps to bring the tissue to be treated into intimate contact with electrodes 28 and viewing window 29. While watching through viewing window 29, the operator actuates switch 62, electrically connecting electrodes 28 to RF generator 14 through conductors 18. Electric current then passes through the diseased tissue positioned in viewing window 29. When the operator observes that the tissue in viewing window 29 has been ablated sufficiently, the operator deactuates switch 62 to stop the ablation. The operator may reposition electrodes 28 for subsequent tissue treatment, or may withdraw ablation cap 26 (together with flexible endoscope 12). As illustrated in FIG. 6, treated tissue 56 has substantially the same width and length as viewing window 29.

Figure 7:
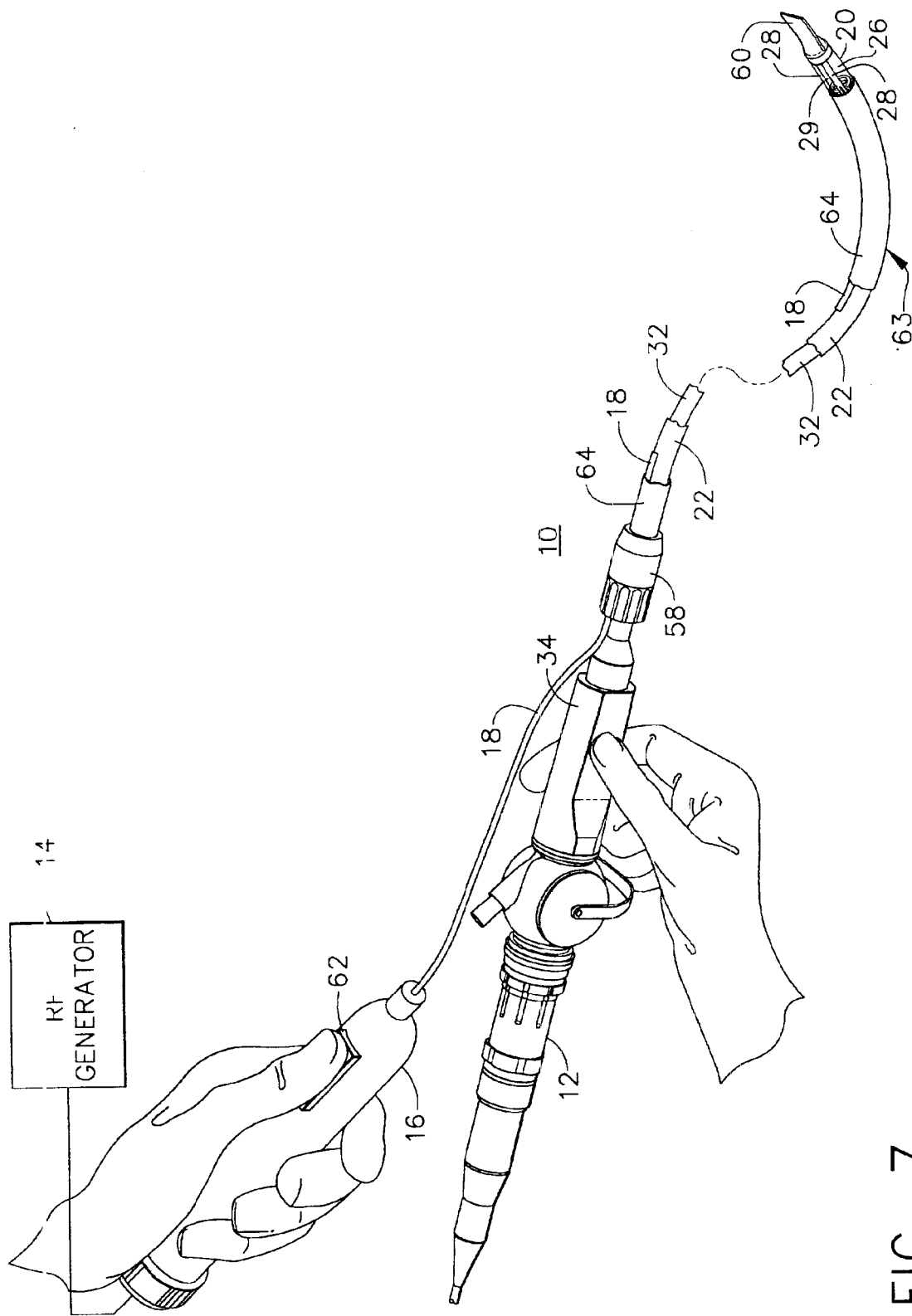
FIG. 7 illustrates an alternative embodiment of an endoscopic ablation system, which includes a rotation knob 58 and a valve 60 (also referred to as a tapered end cover).

FIG. 7 shows an alternate embodiment of an endoscopic ablation system 10 and generally comprises an ablation cap 20, a sheath 63, a pair of conductors 18, a handpiece 16 having a switch 62, and an RF generator 14. An operator may rotate ablation cap 20 around flexible shaft 32 of flexible endoscope 12 by manipulation of a rotation knob 58, which connects to sheath 63. Ablation cap 20 includes a rigid support member 26, at least two electrodes 28, and at least one viewing window 29 (between each pair of adjacent electrodes). Sheath 63 comprises a rotation tube 22 covered by an external tube 64. Ablation cap 20 attaches directly to the distal end of sheath 63. Rotation tube 22 is made from a stiff tube material such as, for example, corrugated polyethylene tubing, and fits slidably over a conventional, flexible endoscope. External tube 64 is preferably made from a heat-activated shrink tube material such as polyolefin. Conductors 18 are spirally wrapped around rotation tube 22 prior to assembling and shrinking external tube 64 onto rotation tube 22, thereby tightly retaining conductors 18 in the wound configuration. In the embodiment shown in FIG. 7, a valve 60 (also referred to as a tapered end cover), which may be, for example, a duck bill valve, connects to the distal end of rigid support member 26. Valve 60 allows an operator to extend the distal end of flexible endoscope 12 beyond the distal end of rigid support member 26 to improve visualization of tissue structures, especially during intubation. The operator may also retract the distal end of flexible endoscope 12 within rigid support member 26 to allow visualization of viewing window 29 and electrodes 28, while preventing bodily fluids from entering rigid support member 26 and impairing visualization by contact with flexible endoscope 12.

Alternate embodiments of valve 60 may be envisioned by those skilled in the art, each embodiment being particularly adapted to the medical procedure and anatomical structures involved. For example, in an alternative embodiment of the present invention, the distal end of valve 60 could be further tapered and elongated to allow for easier insertion into the esophagus. Valve 60 could further be transparent to enable the physician to visualize through valve 60 during intubation into the esophagus, while preventing contact of bodily fluids against the distal end of flexible endoscope 12.

FIG. 8 is a sectional view taken along the longitudinal axis of endoscopic ablation system 10 of FIG. 7. The distal portion of flexible shaft 32 is inside rotation tube 22 of endoscopic ablation system 10. A pair of conductors 18 passes through a strain relief 66 of rotation knob 58 and between external tube 64 and rotation tube 22. Each conductor 18 connects electrically to one of electrodes 28 on ablation cap 20. Rotation tube 22 rotatably joins rotation knob 58 to ablation cap 20, enabling the operator to rotatably orient electrodes 28, even after insertion into the esophagus, by remotely actuating rotation knob 58. The distal end of flexible shaft 32 extends from the distal end of sheath 63 into ablation cap 20 and proximal to electrodes 18. A viewing window 29 between electrodes 28 is within the field of view of flexible endoscope 12, thus enabling the operator to see on a display monitor the tissue that is located between electrodes 18. Valve 60 extends from the distal end of ablation cap 20 to prevent tissue or fluids from entering ablation cap 20.

FIG. 9 is a sectional view taken along line 9-9 of ablation cap 20 of endoscopic ablation system 10 of FIG. 8. Conductors 18 connect to electrodes 28 with the portion of rigid support member 26 between electrodes 28 defining viewing window 29. Rotation tube 22 retains flexible shaft 32. The inside diameter of rotation tube 22 is larger than the outer diameter of flexible endoscope 12 to allow rotation of rotation tube 22 while holding flexible endoscope 12 stationary, or vice versa. In this embodiment at least the portion of rigid support member 26 that forms viewing window 29 is transparent so that the operator may endoscopically view the tissue between electrodes 28. Flexible endoscope 12 includes a light source 40, a viewing port 38, and a working channel 36.

FIG. 10 is a sectional view taken along line 10—10 of rotation tube 22 of endoscopic ablation system 10 of FIG. 8. External tube 64 and rotation tube 22 assemble and retain conductors 18 as already described. Light source 40, viewing port 38, and working channel 36 of flexible endoscope 12 are shown.

Figure 11:
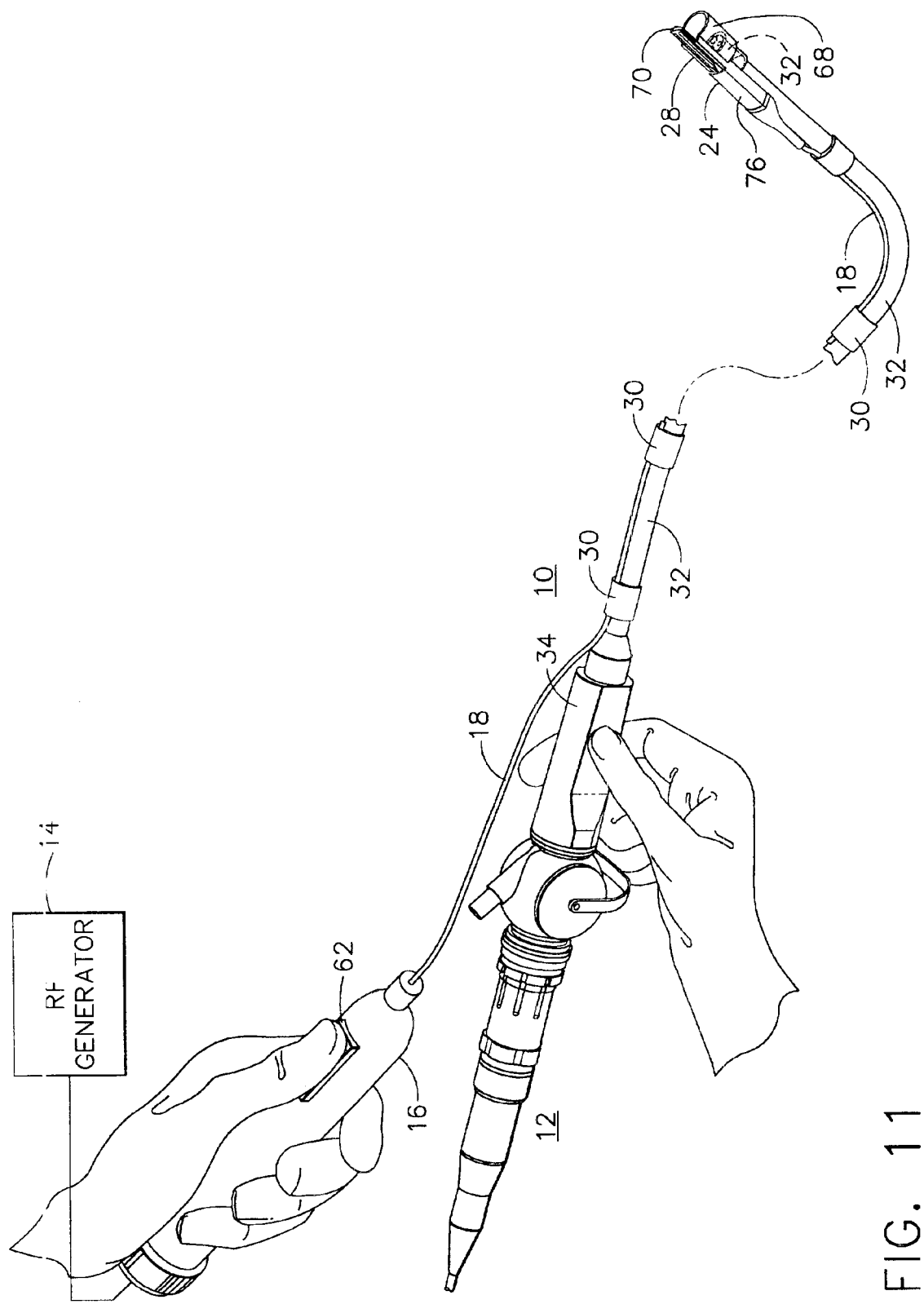
FIG. 11 is an illustration of a further embodiment of an endoscopic ablation system, which includes an electrode sled 70.

FIG. 11 shows a further embodiment of an endoscopic ablation system 10 according to the present invention. A flexible ablation cap 24 includes a flexible support member 68 and at least two electrodes 28 mounted on an electrode sled 70, which may be housed in or extended from a sled housing 76. Flexible ablation cap 24 mounts over the distal end of flexible shaft 32. Conductors 18 electrically connect to electrodes 28 as in the previous embodiments, and may be attached to flexible shaft 32 by a plurality of clips 30. Again, conductors 18 electrically connect to RF generator 14 by a switch 62 of a handpiece 16.

Figure 12:
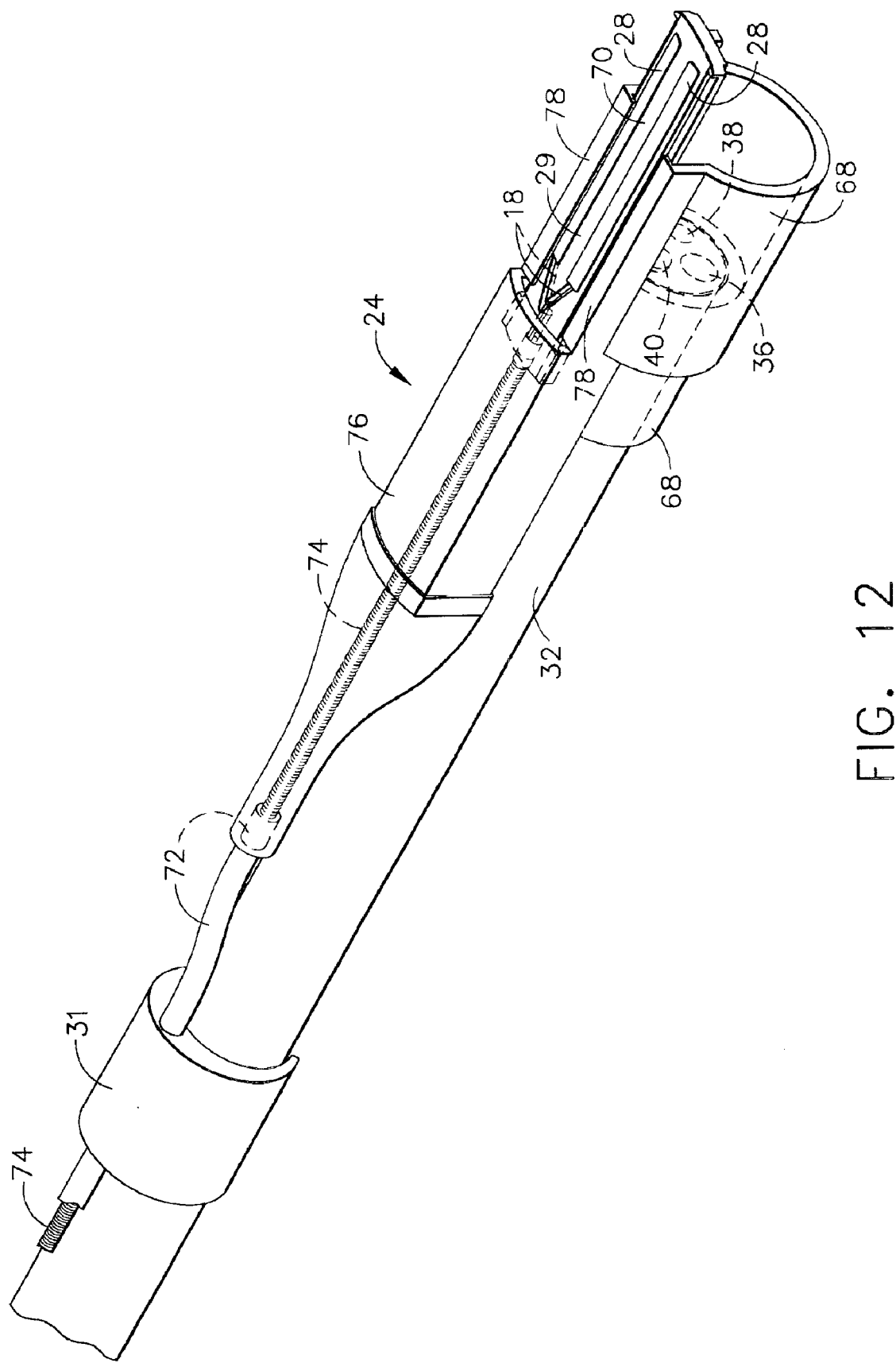
FIG. 12 is an enlarged, perspective view of the distal portion of the endoscopic ablation system illustrated in FIG. 11, showing electrode sled 70 in an extended position.

FIG. 12 is an enlarged view of flexible ablation cap 24 of the endoscopic ablation system 10 illustrated in FIG. 11 with electrode sled 70 fully extended. A sled housing 76 is a soft and flexible, pouch-like container, which may be made of a material such as PTFE in order to prevent damage to the mucosa as the operator introduces endoscopic ablation system 10 into the esophagus. Sled housing 76 and flexible support member 68 may be molded as a single piece. Electrode sled 70 may be made of a clear rigid material such as, for example, polycarbonate. As shown in FIG. 12, electrode sled 70 includes two electrodes 28, a viewing window 29, and two conductors 18. At least the portion of electrode sled 70 that forms viewing window 29 is transparent to allow the operator to view endoscopically the tissue between electrodes 28. Flexible support member 68 includes sled guides 78, which are adapted to receive electrode sled 70. Extension of sled 70 to an extended position stiffens flexible support member 68 such as may be desired during ablation; retraction of sled 70 to a retracted position allows flexible support member 68 to flex such as may be desirable during intubation. A drive cable 74, which retains conductors 18, extends proximally through sled housing 76 and into a sleeve 72. Sleeve 72 attaches to flexible shaft 32 by a fixed clip 31. Thus, by extending drive cable 74, electrode sled 70 moves distally and, by retracting drive cable 74, electrode sled 70 moves proximally into sled housing 76.

Figure 13:
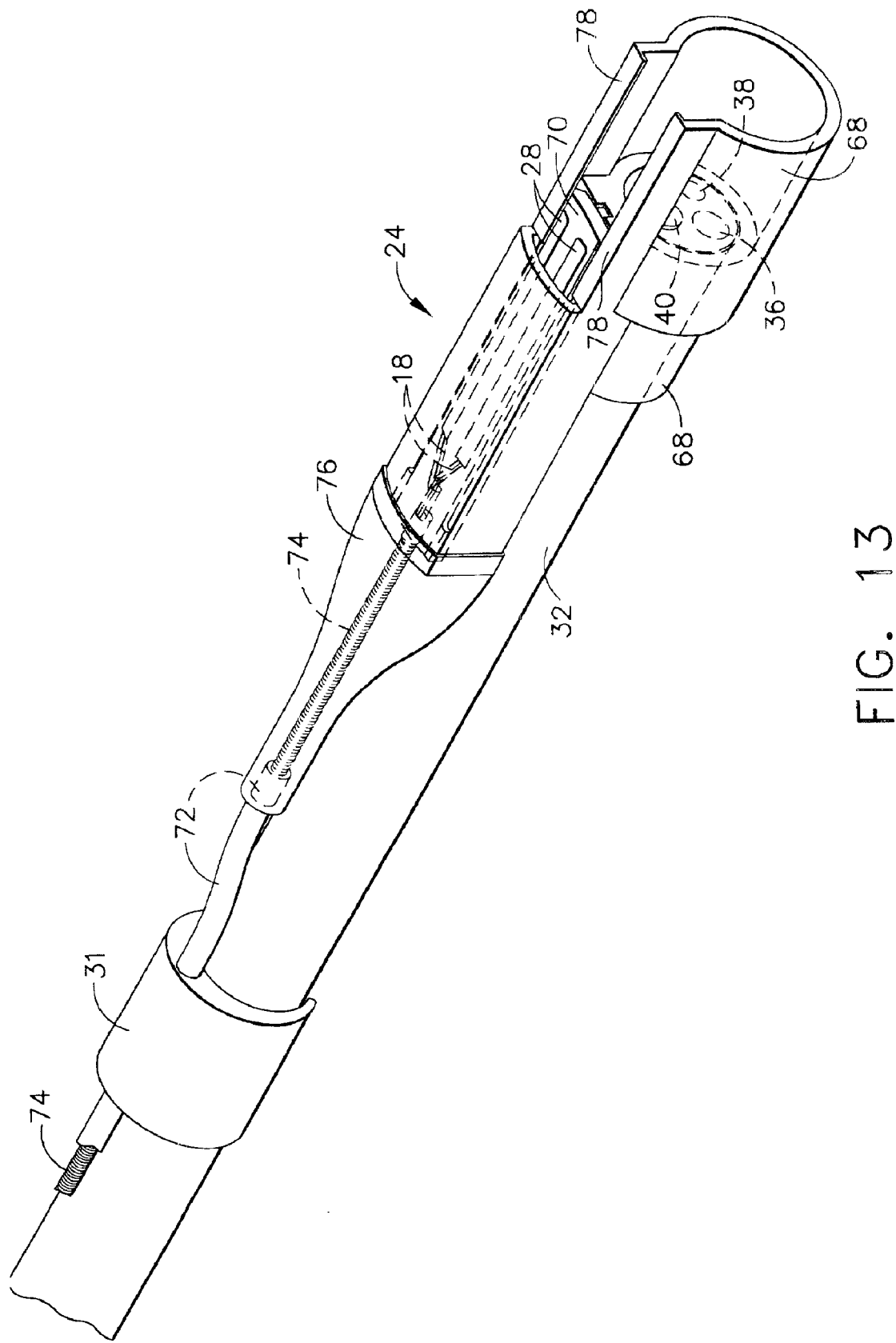
FIG. 13 is an enlarged, perspective view of the distal portion of the endoscopic ablation system illustrated in FIG. 11, showing electrode sled 70 in a retracted position.

FIG. 13 shows flexible ablation cap 24 of endoscopic ablation system 10 of FIG. 11 with electrode sled 70 retracted into sled housing 76, or in a retracted position.

Figure 14:
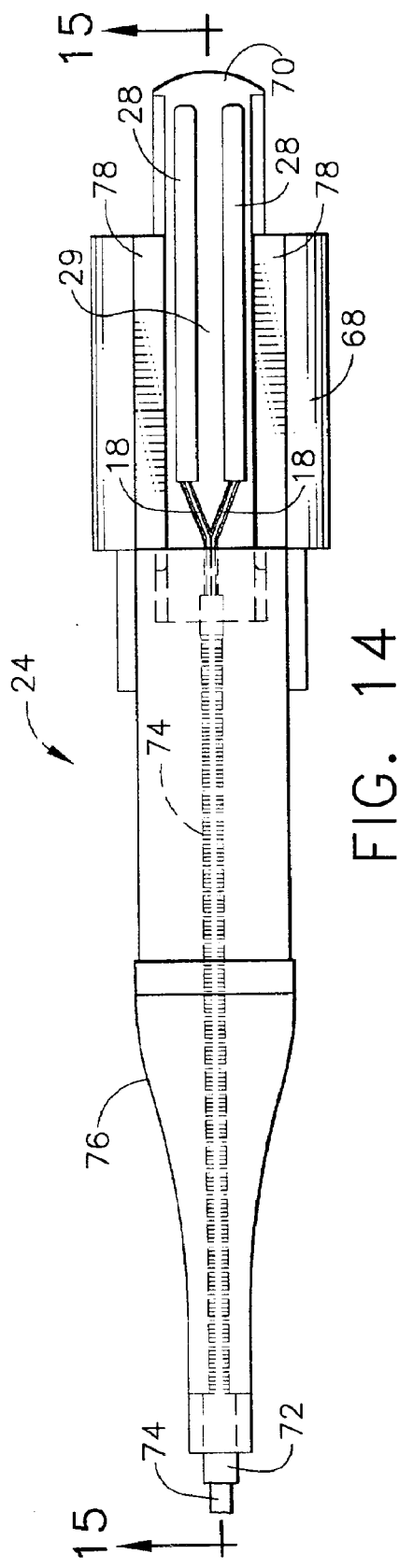
FIG. 14 is an enlarged, top view of the distal portion of the endoscopic ablation system illustrated in FIG. 11, showing electrode sled 70 in the extended position.
Figure 15:
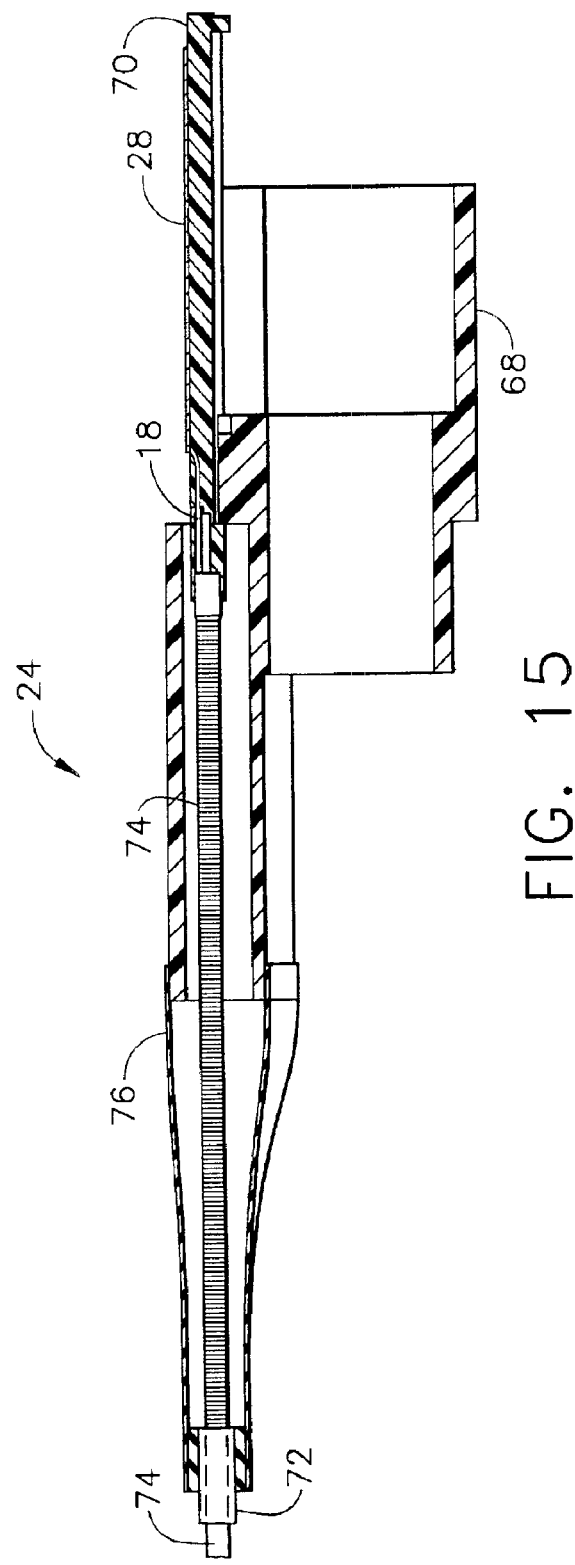
FIG. 15 is an enlarged, sectional side view of the distal portion of the endoscopic ablation system illustrated in FIG. 11, showing electrode sled 70 in the extended position.
Figure 16:
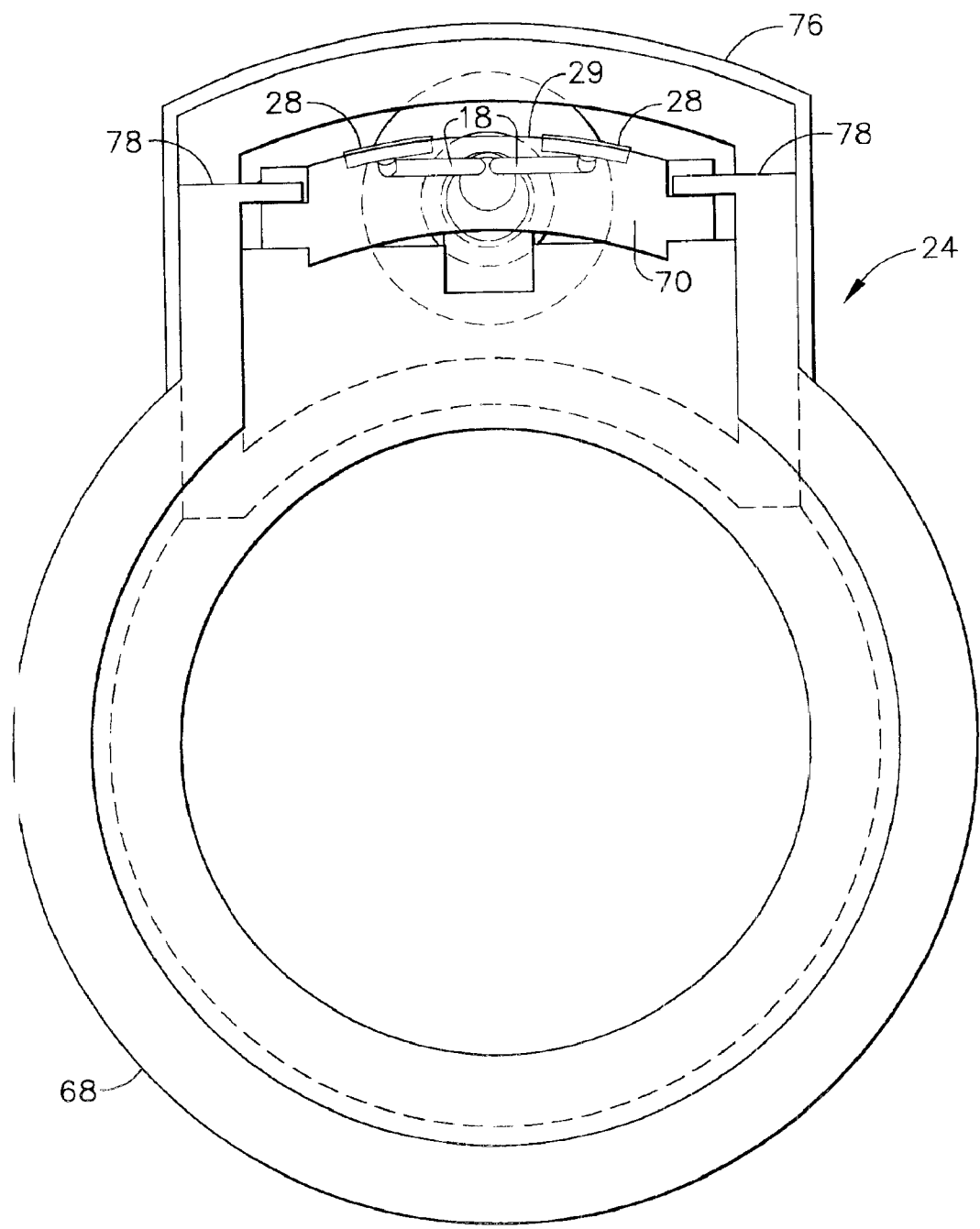
FIG. 16 is an enlarged, end view of the distal portion of the endoscopic ablation system illustrated in FIG. 11.

FIGS. 14–16 are additional views of flexible ablation cap 24 illustrated in FIG. 11. FIG. 14 is a top view of flexible ablation cap 24 with electrode sled 70 in an extended position. FIG. 15 is a sectional view taken at line 15—15 of FIG. 14 of flexible ablation cap 24 with electrode sled 70 in an extended position. In FIGS. 14 and 15 electrode sled 70 includes electrodes 28, viewing window 29 and conductors 18, which are connected to electrodes 28. Flexible support member 68 includes sled guides 78. Drive cable 74, which houses conductors 18, is in turn housed within sled housing 76 and extends proximally into sleeve 72. FIG. 16 is an end view of the flexible ablation cap 24 of the endoscopic ablation system 10 illustrated in FIG. 11. FIG. 16 illustrates the arrangement of sled guides 78 and the engagement of electrode sled 70 by sled guides 78.

Figure 17:
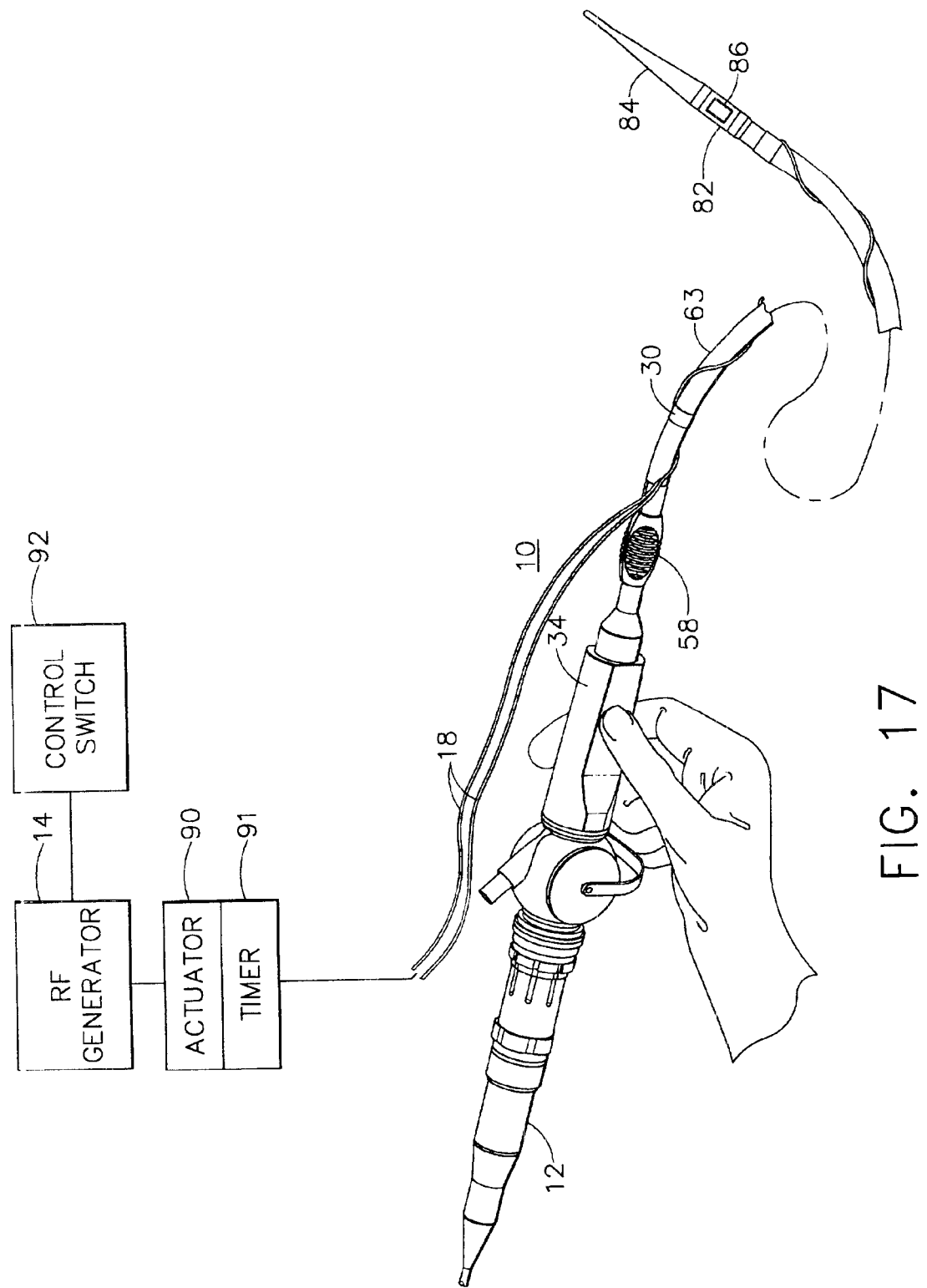
FIG. 17 is an illustration of a further embodiment of an endoscopic ablation system, which includes a tapered end cover 84 and a timer 91.

FIG. 17 is an illustration of a further embodiment of an endoscopic ablation system 10 for use with an endoscope 12 having an endoscope handle 34. Endoscopic ablation system 10 generally comprises a rotation knob 58, a sheath 63, an ablation cap 82, and a tapered end cover 84. Ablation cap 82 further includes an ablation cap-opening 86. Conductors 18 spirally wrap around the outside of sheath 63 in this embodiment, and at least one clip 30 attaches conductors 18 to sheath 63. Endoscopic ablation system 10 further comprises an actuator 90 and a timer 91. A plurality of electrodes 28 (hidden in this view) on ablation cap 82 electrically connect, via a pair of conductors 18, to actuator 90. The operator actuates actuator 90 manually to enable timer 91 to electrically connect electrodes 28 to RF generator 14 for a predetermined period of time. The operator then actuates control switch 92, which may be a foot operated control switch commonly available with RF generators, to activate RF generator 14. When RF generator 14 is activated, timer 91 automatically connects RF generator 14 to electrodes 28 for a predetermined length of time. For the embodiments of an endoscopic ablation system described herein, an appropriate predetermined length of time is approximately in the range of 0.1 to 10 seconds, and is preferably about one second. However, the length of predetermined time may vary depending on the geometry of the electrodes, the power level used on the RF generator, the type of tissue being treated, and other factors. Timer 91 includes a conventional timer circuit that is connected in electrical series to the output of a RF generator 14 having a control switch 92. When the operator actuates control switch 92, the electrical current from RF generator 14 induces a secondary current inside of timer 91. This secondary current supplies and immediately activates the timer circuit of timer 91, thereby connecting the output of RF generator 14 to electrodes 28 via a relay inside of timer 91. After a predetermined period of time, the relay disengages automatically, therefore electrically disconnecting RF generator 14 from the electrodes 28. Therefore, the operator controls when electrodes 28 are energized to begin ablation of tissue, but timer 91 controls when ablation stops, even though the operator may still be activating control switch 92. Timer 91 ensures complete ablation of diseased tissue in the viewing window and greatly reduces the possibility of operator error associated with RF energy application.

Timer 91 and actuator 90 of FIG. 17 may be provided as a handle with a switch much like handle 16 and switch 62 of FIG. 1. Alternately, timer 91 and actuator 90 may be incorporated into a table top unit (not shown), combined with RF generator 14 and control switch 92, or electronically packaged in many other ways that are readily apparent to one skilled in the art. Actuator 90, timer 91, RF generator 14, and control switch 92 may comprise a reusable portion of endoscopic ablation system 10. The remaining portion that includes conductors 18, sheath 63, rotation knob 58, and ablation cap 82 may be provided, for example, as a relatively low cost, sterile device that is disposable after use on one patient.

Figure 18:
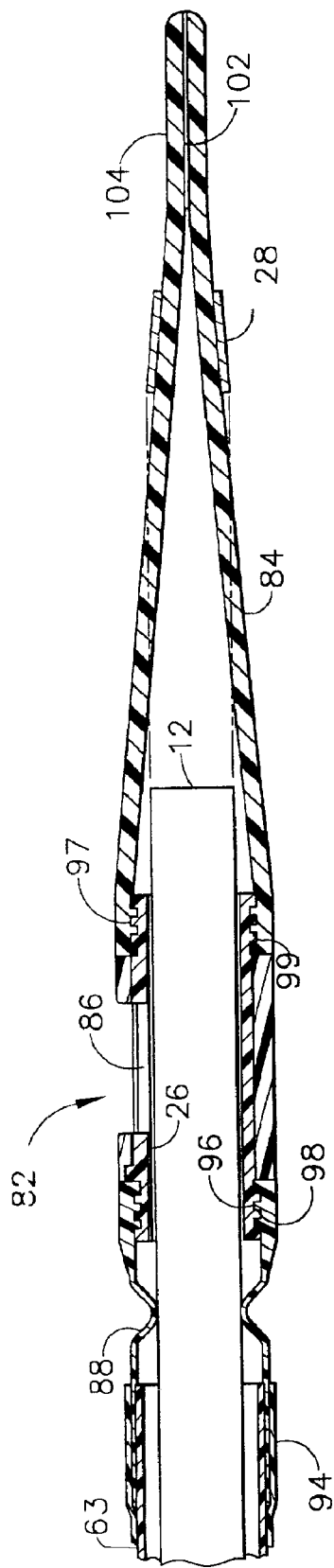
FIG. 18 is a sectional view of the distal portion of the endoscopic ablation system shown in FIG. 17, wherein a plurality of electrodes 28 are mounted on the tapered end cover 84 near a distal tip 104.
Figure 19:
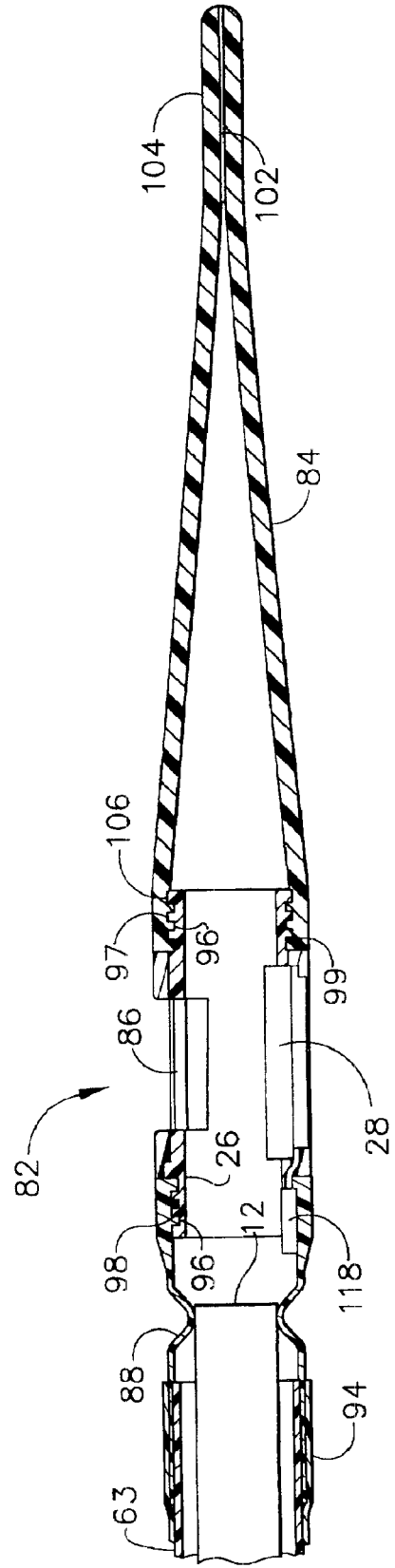
FIG. 19 is a sectional view of the distal portion of the endoscopic ablation system shown in FIG. 17, wherein a plurality of electrodes 28 are mounted on a rigid support member 26.
Figure 20:
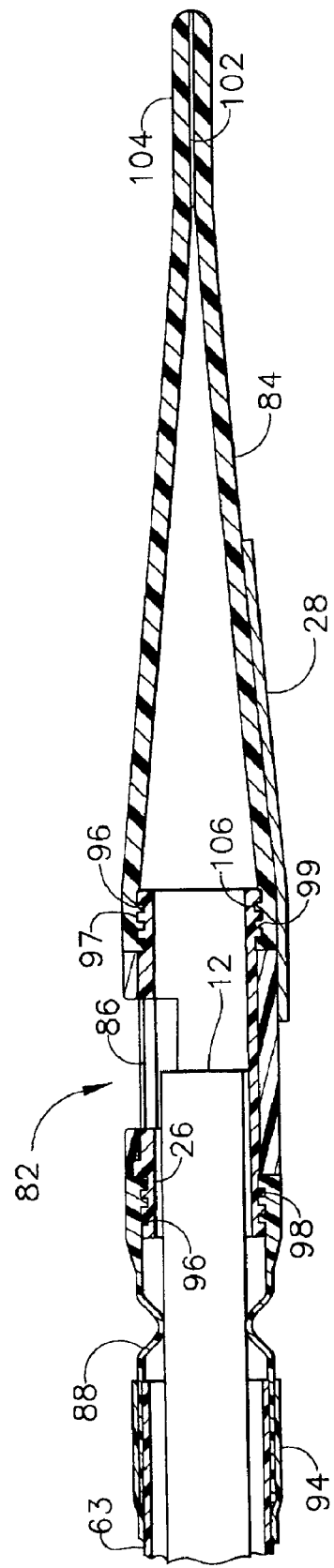
FIG. 20 is a sectional view of the distal portion of the endoscopic ablation system shown in FIG. 17, wherein a plurality of electrodes 28 are mounted partially on rigid support member 26 and partially on tapered end cover 84.

FIGS. 18, 19, and 20 are sectional views of the distal portion of endoscopic ablation system 10 shown in FIG. 17, and illustrate alternate locations of electrodes 28. FIGS. 18, 19, and 20 show the distal end of sheath 63 inserted into the proximal end of a flexible coupling 88 and attached by a ring 94 tightly compressed around sheath 63 and the proximal end of flexible coupling 88. The distal end of flexible coupling 88 attaches to the proximal end of a rigid support member 26 of ablation cap 82 by the engagement of a plurality of annular projections 96 on the inside of the distal end of flexible coupling 88 with a like plurality of annular grooves 98 formed into the proximal end of rigid support member 26. Flexible coupling 88 is made of a flexible tube material such as silicone rubber and allows low force angulation of sheath 63 with respect to ablation cap 82, thus facilitating passage of ablation cap 82 through the esophagus of the patient. The distal end of rigid support member 26 includes a plurality of annular grooves 99 for retaining a plurality of annular projections 97 on the inside of the proximal end of tapered end cover 84. Tapered end cover 84 is made of a transparent, flexible material such as, for example, clear or tinted polyurethane that is commonly used for flexible, extruded tubing. Tapered end cover 84 further includes an elongated, distal tip 104 that helps the operator to insert ablation cap 82 into the esophagus.

Tapered end cover 84 is hollow in order to allow positioning of the distal end of endoscope 12 partially into tapered end cover 84, as shown in FIG. 18. This enables the operator to view the interior of the esophagus, yet protects the distal end of endoscope 12 from tissue structures and bodily fluids that may impair visualization. Tapered end cover 84 is shaped like a bougie tube, which is commonly used by endoscopists for dilating the esophagus prior to intubation with an endoscope. Distal tip 104 of tapered end cover 84 includes a channel 102 so that the operator may pass a guide wire through ablation cap 82 and sheath 63, in order to facilitate positioning of ablation cap 82 inside of the esophagus. Gastroenterologists commonly use a guide wire that is inserted into the esophagus to guide, for example, a dilating instrument into the esophagus.

As shown in FIGS. 18, 19, and 20, electrodes 28 may be mounted at varying locations on ablation cap 82. In FIG. 18, electrodes 28 are attached to the outside of tapered end cover 84 near distal tip 104. As indicated in FIG. 18, electrodes 28 are positioned on a portion of tapered end cover 84 that has a smaller cross-sectional diameter than the diameter of the distal end of endoscope 12. As shown in FIG. 19, electrodes 28 may also be attached to rigid support member 26, as was also described for the embodiments shown in FIGS. 1 and 7. In FIG. 19, a portion of one of conductors 18 is shown as it may be electrically connected to one of electrodes 28 by a solder and/or compression connection. (Conductors 18 are not shown in FIGS. 18 and 20.) In FIG. 20, electrodes 28 are positioned partially on rigid support member 26 and partially on tapered end cover 84. Electrodes 28 may vary in size, shape, and position on ablation cap 82, as shown in the examples of FIGS. 18, 19, and 20, but importantly, still follow the geometric relationships described for FIG. 3 in order to achieve a desired ablation quality.

Still referring to FIGS. 18, 19, and 20, rigid support member 26 also includes side opening 86. In the examples shown, side opening 86 is rectangularly shaped and positioned between the distal end of flexible coupling 88 and the proximal end of tapered end cover 84. In the examples shown in FIGS. 19 and 20, side opening 86 is on the side of rigid support member 26 opposing the position of electrodes 26. Side opening 86 can be positioned substantially 180 degrees opposite of the viewing window 29. Side opening 86 provides access to tissue structures next to ablation cap 82 with instrumentation passed through the working channel of endoscope 12. In addition, side opening 86 allows fluid communication between endoscope 12 (that normally includes suction and irrigation channels) and the interior of the esophagus around ablation cap. Therefore, the operator may position electrodes 28 adjacent to tissue to be ablated and apply the suction provided with endoscope 12. As the lumen size of the esophagus decreases under vacuum, the esophagus collapses around ablation cap 82, thus bringing the tissue to be treated in intimate contact with electrodes 28 and viewing window 29. This facilitates uniform electrode contact for even ablation, and improves endoscopic visualization through the viewing window of tissue being treated during the procedure.

It is believed that support member 26 can aid in stabilizing the shape of the lumen (such as the esophagus) during a medical procedure, such as ablation. In particular, the tissue of the esophagus can conform to the outside shape of the rigid support member 26, to help ensure contact of the ablation electrodes with the tissue to be treated. In addition, it is believed that the side opening 86 can assist in stabilizing the shape of the esophagus and ensuring proper contact of electrodes or other ablation device with the tissue to be treated.

The side opening 86 can be operatively associated with suction, such as by being in flow communication with a vacuum source. For instance, a vacuum can be communicated to the side opening 86 through sheath 63 or through a vacuum device associated with an endoscope such as endoscope 12. As described above, suction provided through side opening 86 can assist in collapsing the esophagus around the support member 26 to assist in conforming the tissue of the esophagus to the outside surface of the support member and into contact with ablation electrodes, such as electrodes 28.

In some treatment applications, folds or other irregularities in the tissue of the lumen being treated may make it difficult to access tissue to be treated. For instance, the folds or irregularities in the tissue of the esophagus may result in circumferential expanse of esophageal tissue which is substantially larger than the circumference of the outside surface of the support member 26. In order to provide suitable contact of the tissue to be treated with ablation electrodes, the support member 26 can be positioned in the esophagus where treatment is desired, and suction communicated through side opening 86 to draw the tissue into contact with the support member 26. With suction activated, the support member 26 can be rotated about it's central axis. Such rotation can be through an angle sufficient to pull on the tissue, such as in a generally circumferential direction and generally tangential to esophageal tissue at the side opening 86. The rotation can be used to draw on and straighten or otherwise extend at least a portion of the folds or irregularities in the esophagus to provide a relatively flat tissue surface as viewed through viewing window 29. The electrodes 28 can then be activated to treat the tissue visible in viewing window 29. The electrodes can be deactivated upon proper ablation of the tissue. The suction can be deactivated as need to reposition the support member 26 in the esophagus. The procedure can be repeated in incremental steps around the circumference of the esophagus to provide treatment as needed.

Side opening 86 provides a further benefit in that one or more additional instruments can be introduced through the sheath or endoscope to access tissue through side opening 86. For example, a tissue forceps device can be advanced through the sheath or through an endoscope within the sheath to access tissue and obtain a tissue sample through the side opening 86. Alternatively, a separate electro-cautery device could be used to ablate tissue exposed through side opening 86. In still another embodiment, a support member 26 having a side opening 86 can be provided without electrodes 28, and ablation can be provided with a separate electrode assembly, such as an electrode assembly advanced through the sheath 63 or the endoscope.

Figure 21:
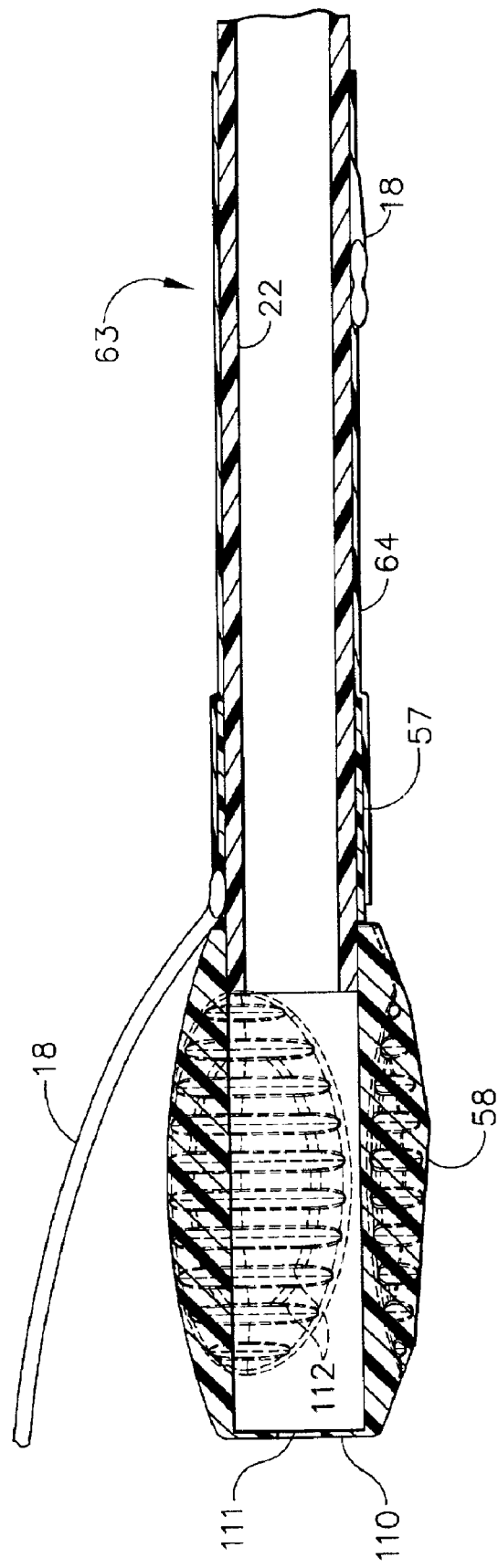
FIG. 21 is a sectional view of the proximal portion of the endoscopic ablation system shown in FIG. 17.

FIG. 21 is a sectional view of the proximal portion of sheath 63, rotation knob 58, and conductors 18 of the endoscopic ablation system 10 shown in FIG. 17. Rotation knob 58 is molded from a flexible material such as a biocompatible rubber. The proximal end of rotation knob 58 includes a proximal seal 110 having a hole 111 for insertion of endoscope 12 (not shown). The interior of the sheath distal to proximal seal 110 and the interior of ablation cap 82 define an enclosure that is in fluid communication with the interior of the esophagus and the aspiration means of the flexible endoscope 12. Proximal seal 110 prevents fluid communication between the air external to the patient and the interior of sheath 63 and the interior of ablation cap 82. This allows the technique described for FIGS. 18, 19, and 20 for using the suction available with endoscope 12 to pull the interior of the esophagus into intimate contact with electrodes 28 and viewing window 29. Seal 110 also wipes bodily fluids from the exterior of endoscope 12 as it is withdrawn from sheath 63. Rotation knob 58 also includes a distal cylindrical extension 57 that fits tightly over the proximal end of a rotation tube 22 of sheath 63. An external tube 64 fits tightly over the entire length of sheath 63, including the portion attached to distal cylindrical extension 57 of rotation knob 58. Rotation tube 22 may be made of any one of a number of flexible tubing materials, including corrugated polyethylene tubing. External tube 64 is preferably made from polyolefin that is shrink-wrapped tightly onto rotation tube 22 by the application of heat during assembly. In FIG. 21, conductors 18 are shown wrapped around the outside of sheath 63. Conductors 18 may also be assembled between rotation tube 22 and external tube 64 so that the outside of sheath 63 is relatively smooth for passage into the esophagus. Rotation knob 58 also includes a plurality of grip projections 112 to facilitate manipulation.

Figure 22:
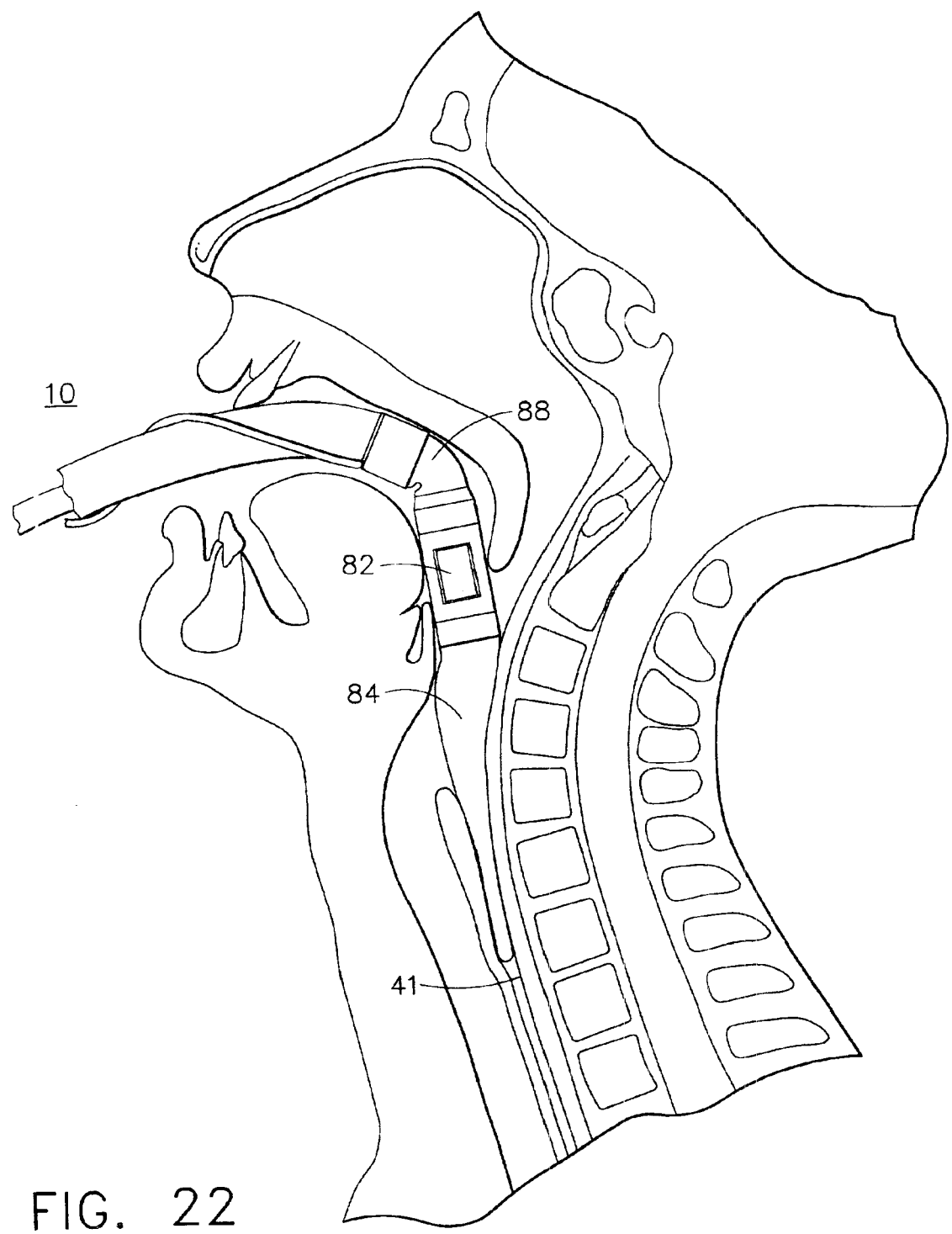
FIG. 22 is a sectional view of the mouth and throat of a patient during intubation of the endoscopic ablation system shown in FIG. 17.

FIG. 22 shows the distal portion of endoscopic ablation system 10 of FIG. 17 partially inserted into the esophagus 41 of a patient. Tapered end cover 84 dilates esophagus 41 as the operator gently inserts ablation cap 82 for positioning near tissue to be ablated. Flexible coupling 88 flexes as shown, reducing the required insertion force and minimizing trauma (and post-procedural pain) to the patient.

Figure 23:
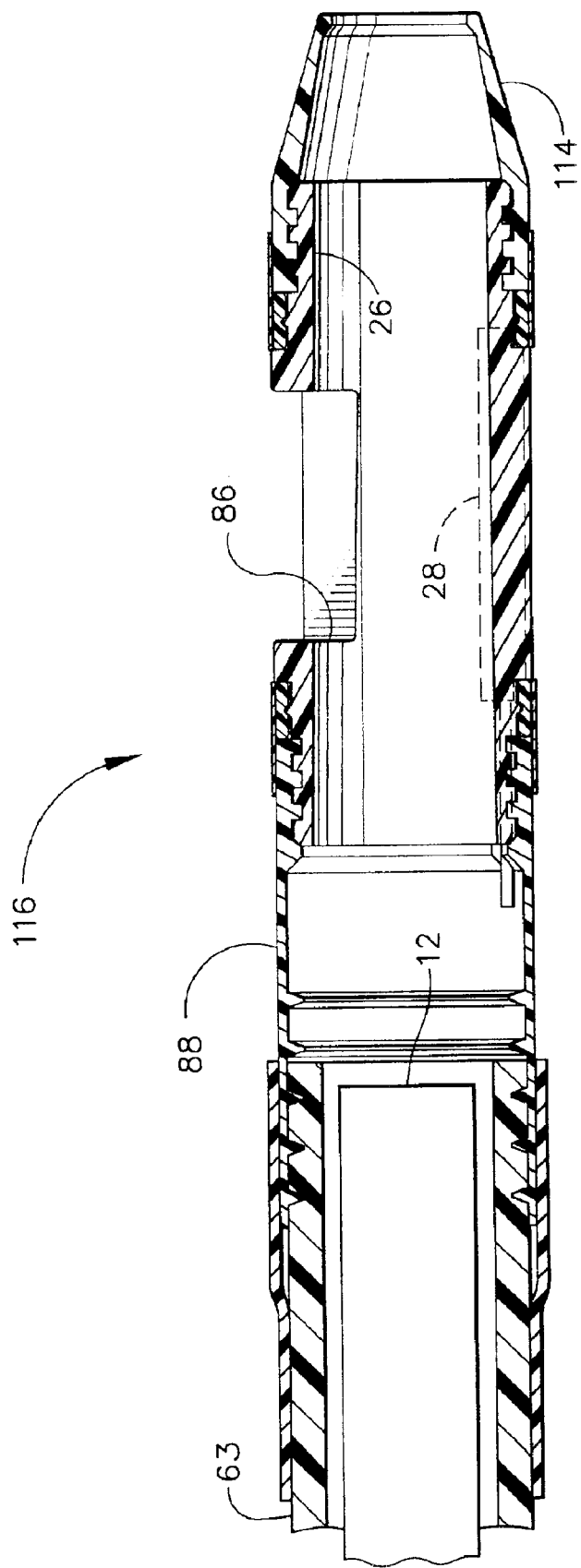
FIG. 23 is a sectional view of the distal portion of a further embodiment of an endoscopic ablation system, which includes an open-end piece 114 (also referred to as a tapered end cover).

FIG. 23 is a sectional view of the distal portion of a further embodiment of an endoscopic ablation system 10. FIG. 23 shows an endoscope 12 inserted into an ablation cap 116 that includes a sheath 63, a plurality of electrodes 28, and a flexible coupling 88 such as was described for FIG. 19. However the embodiment in FIG. 23 includes an open-end piece 114 (also referred to as a tapered end cover) attached to the distal end of rigid support member 26. Open-end piece 114 resembles tapered end cover 84 of FIG. 17, but with all but the proximal portion cut off perpendicular to the longitudinal axis. The remaining taper of open-end piece 114 facilitates passage through the esophagus and substantially prevents body fluids on the esophageal wall from collecting inside ablation cap 116. Open-end piece 114 is made preferably from a flexible material such as silicone rubber. The operator may extend the distal end of endoscope 12 through open-end piece 114, to facilitate endoscopic visualization during intubation of ablation cap 116 into the esophagus. The operator may retract endoscope 12 to a retracted position as shown in FIG. 23 in order to view tissue through a viewing window (not shown) between adjacent electrodes 28, and to watch the progress of ablation.

Now referring again to FIG. 3, the size, shape, and relative position of electrodes 28 are shown, as they would be mounted on rigid support member 26. The region between electrodes 28 forms viewing window 29. In an endoscopic ablation system according to the present invention, the size, shape and relative position of electrodes 28 are established by the Ablation Index, I, and:

$$I=P/d \quad (1)$$

Where:

P is the perimeter of electrodes 28 and d is the separation between adjacent edges 8 of electrodes 28.

In the embodiment of the invention illustrated in FIG. 3:

$$I=2(w+L)/d \quad (2)$$

Where:

w is the width of electrodes 28 and

L is the length of electrodes 28.

Suitable ablation indices can be provided wherein: the separation d can be between about 1 mm and about 3 mm; L can be between about 20 mm and about 40 mm; and w can be between about 3 mm and about 8 mm. In particular, d can be less than or equal to about 2 mm. More particularly, electrode size and spacing of d equal to 2 mm, L equal to 30 mm, and w equal to 5 mm can be used to provide an Ablation Index I=35. In another embodiment, an electrode size and spacing of d equal to 2 mm, L equal to 20 mm, and w equal to 5 mm can be used to provide an Ablation Index I=to 25.

Figure 24:
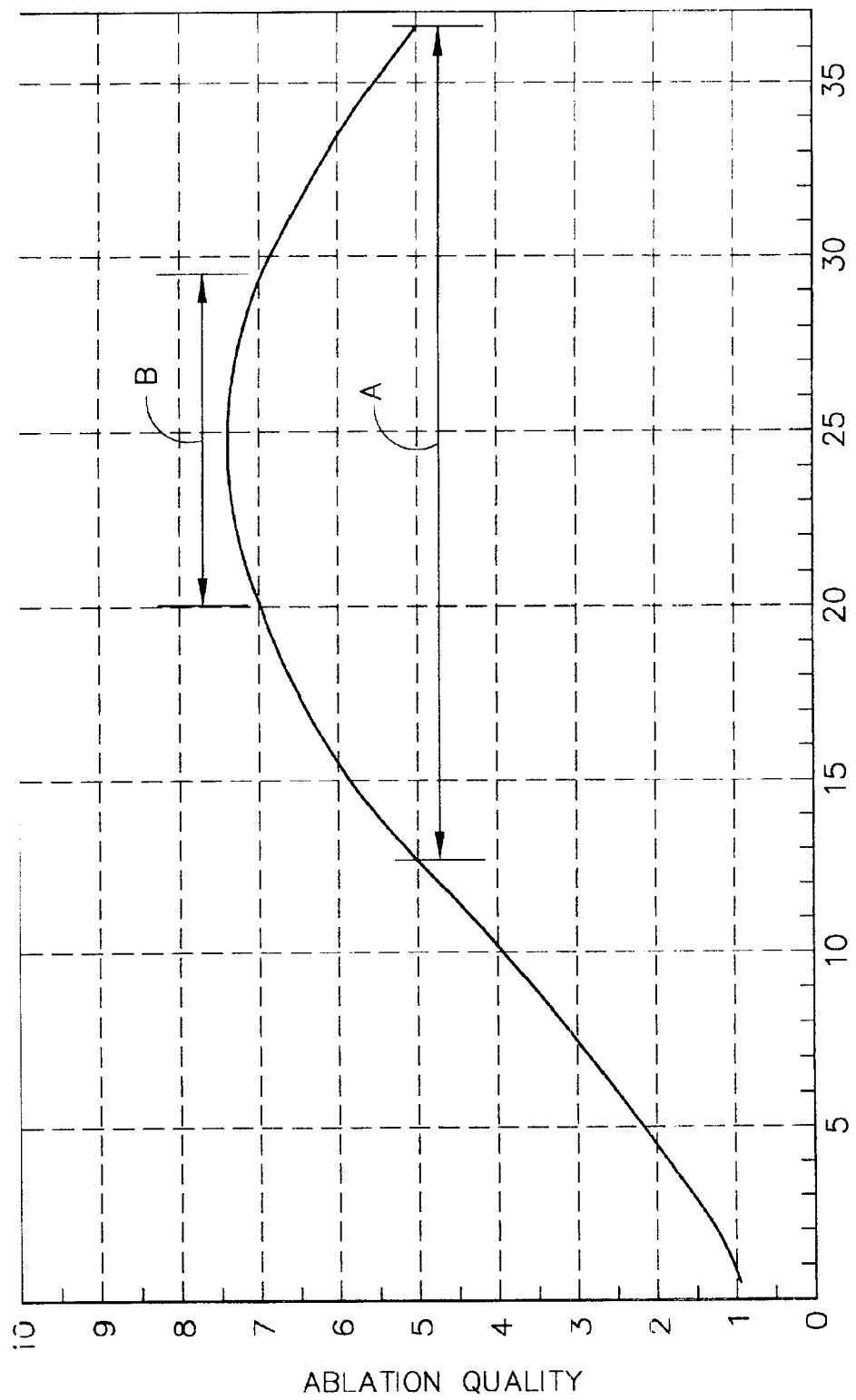
FIG. 24 is a graph showing the relationship of an Ablation Quality to an Ablation Index "I", for the endoscopic ablation system according to the present invention.

Although the electrodes illustrated in FIG. 3 are rectangular in shape, other shapes having an Ablation Index I according to Equation 1 are appropriate for use in the present invention provided that d is substantially constant, i.e. the adjacent edges of the electrodes are substantially parallel and/or equidistanced apart. In an endoscopic ablation system according to one embodiment of the present invention, $1<I<200$ and, preferably, I can be greater than or equal to about 15 and I can be less than or equal to about 35. In FIG. 24, region A includes a range of I from about 13 to about 36.

The graph of FIG. 24 is based on data derived from experiments with different electrode geometries for RF power levels varying between 10 and 50 watts. A pair of mirror image, rectangular electrodes was used for each experiment. The width w was varied between 1–10 mm; the length L was varied between 5–50 mm; the distance d was varied between 1–5 mm. The experiments were performed on soft, muscular porcine tissue having a temperature and moisture content similar to conditions inside the lumen of a human esophagus. For each experiment, the electrodes were brought into intimate contact with the tissue. The time of ablation varied between 1–3 seconds. The RF generator was activated only for the length of time required for at least a portion of the tissue in the viewing window to turn white. The ablated tissue was then sectioned order to approximate ablation depth and to look for uniformity of ablation depth. Two observers then assigned an Ablation Quality, which is a subjective rating of between 1–10. A low Ablation Quality equal to 1 corresponds to an experiment in which ablation occurred only underneath the electrodes and, in some experiments, around the outer edges of the electrode, and not in the tissue between the electrodes. An Ablation Quality of 10 corresponds to an experiment in which ablation occurred only between the electrodes (and visible through the viewing window) and not underneath the electrodes. An Ablation Quality of 5 corresponds to an experiment in which about half of the area under the electrodes was ablated, and about all of the area between the electrodes was ablated. A high Ablation Quality>5 also corresponds to experiments in which the tissue was ablated to a uniform depth of approximately 1 mm. An ablation depth of approximately 1 mm is normally sufficient to destroy diseased tissue in the mucosal and submucosal layers of the human esophagus without damaging the muscular layers of the esophagus.

In FIG. 24, region A indicates the Ablation Index I for when Ablation Quality is greater than or equal to 5 (an average subjective rating) on a scale of 1–10. In some cases, the operator may desire to maintain an ablation index where I is greater than or equal to about 20 and less than or equal to about 28 or 29, as indicated by a region "B" in FIG. 24. Practical considerations related to manufacture, type of tissue being treated, physician preferences, and so on, come into play when determining electrode geometry and selecting an ablation index range. The Ablation Index is used to define an electrode arrangement that substantially confines the initial ablation to the tissue under the viewing window, allowing the operator to control the ablation process. Such an endoscopic ablation instrument will begin to ablate tissue when an electric potential is established between the electrodes (i.e. the electrodes are actuated). However, during the initial ablation process little or none of the tissue directly beneath the electrodes will be ablated and the thermal profile within the treated tissue will have a substantially vertical wall at the edge of the electrodes. Further, the current density of the electrical current flowing between the electrodes will be very high in the tissue under the viewing window, accelerating the ablation of tissue within the treatment region, giving the operator precise control of the treatment region and limiting the ablation of healthy tissue. The operator further has precise control of the degree to which the treated tissue is ablated since the operator may view the entire treatment region through the viewing window. The operator may visually determine when the treated tissue is sufficiently ablated by watching to see when the ablated tissue fills the entire ablation window. When the ablated tissue fills the entire ablation window, the mucosa is consistently ablated to a predetermined depth across the treatment region. The actual depth of the ablation is a function of a number of variables, including power. In one preferred combination, Ablation Index I=25 and RF power equals 30 watts, and the electrodes are energized for 1.3 seconds. Uniform ablation depths of approximately one to two millimeters can be constantly obtainable using the color of the treated tissue in the ablation window as a guide. Ablation depths of one to two millimeters are normally enough to ablate the abnormal tissue in the mucosa without significantly damaging the healthy tissue underneath.

Electrodes having an ablation index and viewing window according to the present invention may be used in other surgical instruments such as, for example, endocutters. Further, electrodes having an ablation index according to the present invention may be used for other treatment regimens such as tissue welding, electrophoresis and coagulation of varicose veins and hemorrhoids. Further, the present invention can be adapted for use in automated surgery, including robot or computer controlled or assisted surgical procedures.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, the endoscopic ablation system of the present invention also has application in robotic-assisted medical procedures. Accordingly, it is intended that only the spirit and scope of the appended claims limit the invention.

What is claimed is:

1. An endoscopic ablation system for electrosurgically treating bodily tissue of a patient, said endoscopic ablation system comprising:

at least two electrodes, each of said electrodes having a perimeter P, and adjacent electrodes have adjacent parallel edges spaced apart by a distance d, wherein an ablation index I=P/d is between approximately 1 and 200;

a viewing window positioned between adjacent electrodes;

an ablation cap for creating space in the lumen of a bodily organ, wherein said at least two electrodes are positioned on said ablation cap, and said viewing window forms a portion of said ablation cap;

a sheath, wherein said ablation end cap is hollow and mounted on the distal end of said sheath, wherein a distal end of a flexible endoscope may be inserted through said sheath and at least partially into said ablation end cap, and said sheath and said ablation end cap are rotatable with respect to said flexible endoscope;

a seal located near the proximal end of said sheath, said seal adapted to allow passage therethrough of the distal end of the flexible endoscope, whereby said sheath and said ablation cap form an enclosure substantially sealed from the air external to the patient; and an RF generator electrically connected to said at least two electrodes, wherein an operator may actuate said RF generator and ablate tissue endoscopically viewable through said viewing window.

2. An endoscopic ablation system according to claim 1, wherein said first and second electrodes have an ablation index I of between 15 and 35.

3. An endoscopic ablation system according to claim 1, wherein said
ablation cap comprises a rigid support member attached to a tapered end cover.

4. An endoscopic ablation system according to claim 3, wherein said tapered end cover is normally closed and is adapted to open in order to allow passage of the distal end of an endoscope therethrough.

5. An endoscopic ablation system according to claim 3, wherein said tapered end cover is made from a transparent, flexible material and is shaped like a bougie tube and is adapted to be passed over a guide wire.

6. An endodcopic ablation system according to claim 1 further including a rotation knob attached at the proximal end of said sheath.

* * * * *